United States Patent [19]

Monn

[11] Patent Number: 5,491,241
[45] Date of Patent: Feb. 13, 1996

[54] BICYCLIC INTERMEDIATES FOR EXCITATORY AMINO ACID RECEPTOR ANTAGONISTS

[75] Inventor: James A. Monn, Indianapolis, Ind.

[73] Assignee: Eli Lilly and Company, Indianapolis, Ind.

[21] Appl. No.: 138,664

[22] Filed: Oct. 18, 1993

[51] Int. Cl.$^6$ .................................................. C07D 209/52
[52] U.S. Cl. .......................... 548/452; 548/251; 548/253
[58] Field of Search .................................. 548/452, 253, 548/251

[56] References Cited

U.S. PATENT DOCUMENTS 4,691,022  9/1987  Henning et al. .
4,999,370  3/1991  Ruger et al. .............................. 548/452

FOREIGN PATENT DOCUMENTS 0383504  8/1990  European Pat. Off. .
9208724  5/1992  WIPO .

OTHER PUBLICATIONS

Zimmerman, D. M. et al, *Trends in Medicinal Chemistry '90*, Oxford (1991), pp. 145–151.

Watkins, J. C., *Can. J. Physiol. Pharmacol.*, (1991), vol. 69, pp. 1064–1075.

Rogawski, M. A., *Drugs*, (1992) vol. 44, No. 3, pp. 279–292.

Ornstein, P. L. et al., *J. Med. Chem.*, (1991), vol. 34, pp. 90–97.

*Primary Examiner*—David B. Springer
*Attorney, Agent, or Firm*—Martin A. Hay; James P. Leeds

[57] ABSTRACT

This invention provides novel bicyclic compounds which are useful as excitatory amino acid receptor antagonists and in the treatment of neurological disorders. This invention also provides intermediates useful in the synthesis of excitatory amino acid antagonists.

6 Claims, No Drawings

BICYCLIC INTERMEDIATES FOR EXCITATORY AMINO ACID RECEPTOR ANTAGONISTS

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate is the most abundant neurotransmitter in the CNS, and mediates the major excitatory pathway in mammals. Glutamate is referred to as an excitatory amino acid (EAA). The receptors that respond to glutamate are called excitatory amino acid receptors (EAA receptors). See Watkins and Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are "ionotropic" excitatory amino acid receptors. This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions. Other neurological conditions, that are caused by glutamate dysfunction, require neuromodulation. These other neurological conditions include muscular spasms, migraine headaches, urinary incontinence, psychosis, opiate tolerance and withdrawal, anxiety, emesis, brain edema, chronic pain, convulsions, and tardive dyskinesia. The use of a neuroprotective agent, such as an NMDA receptor antagonist, is believed to be useful in treating these disorders and/or reducing the amount of neurological damage associated with these disorders. The excitatory amino acid antagonists are also useful as analgesic agents.

Recent studies have shown that NMDA receptor antagonists are neuroprotective in animal models of focal cerebral ischemia. Bullock and Fujisawa, *Journal of Neurotrauma*, 9 (supplement 2), S443 (1992); Scatton et al., *Cerebrovascular Disease*, 1, 121 (1991). These studies have shown that the competitive NMDA antagonist D-(−)CPP-ene provided protection in a focal cerebral ischemia model in cats, the competitive NMDA antagonist CGS 19755 provided protection in a focal cerebral ischemia model in rats, and the competitive NMDA antagonist LY233053 provided protection in a CNS ischemia model in rabbits. Bullock et al., *Journal of Cerebral Blood Flow and Metabolism*, 10, 668 (1990); Simon and Shirasho, *Annals of Neurology*, 27, 606 (1990); Madden et al., *Journal of Neurosurgery*, 76, 106 (1992). The non-competitive NMDA antagonist dizocilpine provided protection in models of focal cerebral ischemia in cats and rats. Park et al., *Journal of Cerebral Blood Flow and Metabolism*, 8, 757 (1988); Park et al., *Annals of Neurology*, 24, 543 (1988). The competitive NMDA antagonist LY274614 is neuroprotective in an animal model of Huntington's Disease. Schoepp, et al., *Journal of Neural Transmission* [General Section], 85, 131 (1991).

These studies strongly suggest that the delayed neuronal degeneration in brain ischemia involves glutamate excitotoxicity mediated at least in part by NMDA receptor activation. Thus, NMDA receptor antagonists will be useful as neuroprotective agents, decreasing the amount of glutamate-induced excitotoxicity and improving the neurological outcome of cerebral ischemia in humans.

Several studies have shown that NMDA antagonists are anticonvulsant agents. Meldrum, Epilepsy Research, 12, 189 (1992); Meldrum, Epilepsia, 32 (supplement 2), S1 (1991); Chapman and Meldrum, New Antiepileptic Drugs (Epilepsy Research Supplement 3), Elsevier, 39 (1991). For example, the competitive NMDA antagonists D-(−)CPP-ene and CGP 37849 are anticonvulsant against sound induced seizures in DBA/2 mice. Chapman, Graham, and Meldrum, *European Journal of Pharmacology*, 178, 97 (1990). Other studies have shown that NMDA antagonists are analgesics. For example, the competitive NMDA antagonist CGS 19755 is analgesic in a warm water tail withdrawal procedure in rhesus monkeys and the competitive NMDA antagonist DL-AP5 was analgesic in a mouse formalin model. France, Winger, and Woods, *Brain Research*, 526, 355 (1990); Murray, Cowan, and Larson, Pain, 44, 179 (1991).

Based on these animal models, NMDA receptor antagonists will be useful in treating acute and chronic neurodegenerative conditions, as well as other conditions that require neuromodulation.

SUMMARY OF THE INVENTION

The present invention provides compounds which are antagonists of the excitatory amino acid receptors. More specifically, the present invention relates to compounds that are antagonists of NMDA excitatory amino acid receptors. The present invention relates to a compound of the formula

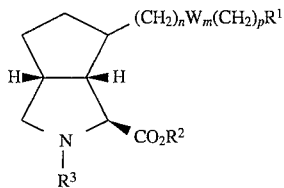

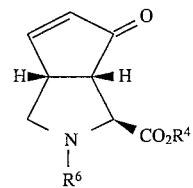

wherein:

W is O or S:

$R^1$ is $CO_2R^2$, $PO_3H_2$, tetrazol-5-yl, or thiotetrazolyl;

$R^2$ is hydrogen, $C_1$–$C_6$ alkyl, substituted alkyl, cycloalkyl, or arylalkyl;

$R^3$ is hydrogen, $C_1$–$C_{10}$ alkyl, arylalkyl, alkoxycarbonyl, aryloxycarbonyl, arylalkoxycarbonyl, or acyl;

n is 0, 1, or 2;

m is 0 or 1;

p is 0 or 1;

provided that when $R^1$ is a thiotetrazolyl group, m is 0;

further provided that the sum of n, m, and p is at least 1;

further provided that when m is 1 and $R^1$ is $CO_2H$, p is 1;

or a pharmaceutically acceptable salt thereof.

The invention also provides pharmaceutical formulations comprising a compound of formula I and a pharmaceutically-acceptable carrier, diluent, or excipient.

Further embodiments of the invention include a method of blocking the NMDA excitatory amino acid receptor, as well as methods of treating a neurological disorder which has been linked to these excitatory amino acid receptors, which comprises administering a compound of formula I. Examples of such neurological disorders which are treated with a formula I compound include cerebral deficits subsequent to cardiac bypass surgery and grafting, stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug-induced Parkinson's Disease, anxiety, emesis, brain edema, chronic pain, or tardive dyskinesia. The formula I compounds are also useful as analgesic agents.

The present invention also relates to compounds that are useful in the preparation of the formula I compounds. More specifically, the present invention relates to a compound of the formula

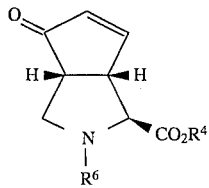

wherein:

$R^4$ is $C_1$–$C_6$ alkyl, substituted alkyl, cycloalkyl, or arylalkyl; and $R^6$ is acyl, alkoxycarbonyl, aryloxycarbonyl, or arylalkoxycarbonyl.

Another aspect of the present invention is a compound of the formula wherein:

$R^4$ is $C_1$–$C_6$ alkyl, substituted alkyl, cycloalkyl, or arylalkyl; and $R^6$ is acyl, alkoxycarbonyl, aryloxycarbonyl, or arylalkoxycarbonyl.

DETAILED DESCRIPTION OF THE INVENTION

In the above formula, the term "$C_1$–$C_{10}$ alkyl" represents a straight or branched alkyl chain having from one to ten carbon atoms. Typical $C_1$–$C_{10}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, and the like. The term "$C_1$–$C_{10}$ alkyl" includes within it the terms "$C_1$–$C_6$ alkyl" and "$C_1$–$C_4$ alkyl". Typical $C_1$–$C_6$ alkyl groups include methyl, ethyl, n-propyl, isopropyl, n-butyl, isobutyl, sec-butyl, t-butyl, n-pentyl, isopentyl, and n-hexyl. Typical $C_1$–$C_4$ alkyl groups include methyl, ethyl, n-propyl, isopropyl, n-butyl, isobutyl, sec-butyl, and t-butyl.

The term "acyl" represents a hydrogen or $C_1$–$C_6$ alkyl group attached to a carbonyl group. Typical acyl groups include formyl, acetyl, propionyl, butyryl, valeryl, and caproyl.

The term "substituted alkyl," as used herein, represents a $C_1$–$C_6$ alkyl group that is substituted by one or more of the following: hydroxy, fluoro, chloro, bromo, and iodo. Examples of a substituted alkyl group include hydroxymethyl, chloromethyl, bromomethyl, iodomethyl, dichloromethyl, dibromomethyl, trichloromethyl, trifluoromethyl, chloroethyl, bromoethyl, perfluoroethyl, 2,2,2-trifluoro-1,1-dichloroethyl, 5-hydroxypentyl, 2-hydroxy-3,3,3-trifluoropropyl, and the like.

The term "$C_1$–$C_4$ alkoxy" represents groups such as methoxy, ethoxy, n-propoxy, isopropoxy, n-butoxy, t-butoxy, and like groups. The term "halogen" refers to the fluoro, chloro, bromo, or iodo groups.

The term "substituted phenyl," as used herein, represents a phenyl group substituted with one or two moieties chosen from the group consisting of halogen, hydroxy, cyano, nitro, $C_1$–$C_6$ alkyl, $C_1$–$C_4$ alkoxy, alkoxycarbonyl, protected carboxy, carboxymethyl, hydroxymethyl, amino, aminomethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 3,4-dimethylphenyl, 4-ethylphenyl, 4-methoxyphenyl, 4-carboxyphenyl, 4-(hydroxymethyl)phenyl, 4-aminophenyl, 4-(methoxycarbonyl)phenyl, 4-(protected carboxy)phenyl, 4-trifluoromethylphenyl, and the like.

The term "aryl" represents groups such as phenyl and substituted phenyl as described above. The term "arylalkyl" represents a $C_1$–$C_4$ alkyl group bearing an aryl group.

Representatives of this latter group include benzyl, 1-phenylethyl, 2-phenylethyl, 3-phenylpropyl, 4-phenylbutyl, 2-methyl-2-phenylpropyl, (4-chlorophenyl)methyl, (2,6-dichlorophenyl)methyl, (4-hydroxyphenyl)methyl, (2,4-dinitrophenyl)methyl, and the like.

The term "cycloalkyl" represents a $C_3$–$C_7$ cyclic alkyl group such as cyclopropyl, cyclobutyl, cyclopentyl, cyclohexyl, and the like.

The term "alkoxycarbonyl" means a carboxyl group having a $C_1$–$C_6$ alkyl group attached to the carbonyl carbon through an oxygen atom. Representatives of this group include t-butoxycarbonyl and methoxycarbonyl.

The term "aryloxycarbonyl" represents a carboxyl group bearing an aryl group attached to the carbonyl carbon through an oxygen atom. Representatives of this group include phenoxycarbonyl, (4-chlorophenoxy)carbonyl, and (3-nitrophenoxy)carbonyl.

The term "arylalkoxycarbonyl" represents a carboxyl group having an arylalkyl group attached to the carbonyl carbon through an oxygen atom. Representatives of this group include benzyloxycarbonyl, 2-phenylethoxycarbonyl, 3-phenylpropoxycarbonyl, and the like. The preferred arylalkoxycarbonyl group is benzyloxycarbonyl.

The term "blocking" refers to a formula I compound acting as an antagonist at one or more excitatory amino acid receptors. The term "excitatory amino acid receptor" refers to ionotropic glutamate receptors, receptors that are directly coupled to the opening of ion channels in the cell membrane of neurons, and to metabotropic glutamate receptors, receptors that are coupled to cellular effectors via GTP-binding proteins. The term "NMDA excitatory amino acid receptor" refers to an ionotropic glutamate receptor that is selectively activated by N-methyl-D-aspartate (NMDA ).

While all the formula I compounds of the present invention are believed to be antagonists of the NMDA excitatory amino acid receptor, certain compounds of the invention are preferred for such use. Preferably, the sum of m, n, and p is less than or equal to three. Representative compounds within this preferred group are 3-aza- 8-(3-carboxypropyl)bicyclo [3.3.0]octane-2-carboxylic acid, 3-aza-8-(3-(1(2)H-tetrazol-5-yl)propyl)bicyclo[3.3.0]octane-2-carboxylic acid, 3-aza-8-(2-(1(2)H-tetrazole- 5-thio)propyl)bicyclo[3.3.0]octane-2-carboxylic acid, 3-aza-8-((1(2)H-tetrazol-5-yl)methoxymethyl)bicyclo[3.3.0]octane-2-carboxylic acid, and 3-aza-8-((1(2)H-tetrazol-5-yl)methylthiomethyl)bicyclo[3.3.0]octane-2-carboxylic acid.

Certain compounds of the present invention are more preferred for use as antagonists of the NMDA excitatory amino acid receptor. More preferably, the sum of m, n, and p is less than or equal to two. Representative compounds within this more preferred group are 3-aza-8-(carboxymethyl)bicyclo[ 3.3.0 ]octane-2-carboxylic acid, 3-aza- 8-(2-carboxyethyl)bicyclo[3.3.0]octane-2-carboxylic acid, 3-aza-8-((1(2)H-tetrazol-5-yl)methyl)bicyclo[ 3.3.0]octane-2-carboxylic acid, 3-aza-8-(2-(1(2)H-tetrazol-5-yl)ethyl)bicyclo[3.3.0]octane-2-carboxylic acid, 3-aza-8-((1(2)H-tetrazole-5-thio)methyl)bicyclo[3.3.0]octane-2-carboxylic acid, 3-aza-8-(2-(1(2)H-tetrazole- 5-thio)ethyl)bicyclo[3.3.0]octane-2-carboxylic acid, 3-aza-8-((1(2)H-tetrazol-5-yl)methoxy)bicyclo[3.3.0]octane-2-carboxylic acid, and 3-aza-8-((1(2)H-tetrazol -5-yl)methylthio)bicyclo [3.3.0]octane-2-carboxylic acid.

Certain compounds of the invention are most preferred for use as antagonists of the NMDA excitatory amino acid receptor. Most preferably, the sum of m, n, and p is one. Representative compounds within this most preferred group are 3-aza-8-((1(2)H-tetrazol-5-yl)methyl)bicyclo[3.3.0]octane-2-carboxylic acid, ethyl 3-aza-8-((1(2)H-tetrazol-5-yl) methyl)bicyclo[ 3.3.0]octane-2-carboxylate, N-methyl-3-aza- 8-((1(2)H-tetrazol -5-yl)methyl)bicyclo[3.3.0]octane-2-carboxylic acid, ethyl N-methyl-3-aza-8-((1(2)H-tetrazol-5yl)methyl)bicyclo[ 3.3.0]octane-2-carboxylate, N-acetyl-3-aza- 8-((1(2)H-tetrazol-5-yl)methyl)bicyclo[3.3.0]octane-2-carboxylic acid, benzyl 3-aza-8-((1(2)H-tetrazol-5yl)methyl)bicyclo[ 3.3.0]octane-2-carboxylate, ethyl N-methoxycarbonyl-3-aza-8-((1(2)H-tetrazol-5-yl)methyl) bicyclo[ 3.3.0]octane-2-carboxylate, 3-aza-8(( 1(2)H-tetrazole- 5-thio)methyl)bicyclo[3.3.0]octane-2-carboxylic acid, ethyl 3-aza-8-((1(2)H-tetrazole-5-thio)methyl)bicyclo[ 3.3.0]octane-2-carboxylate, N-acetyl-3-aza- 8-((1(2)H-tetrazole-5-thio)methyl)bicyclo[ 3.3.0]octane-2-carboxylic acid, ethyl N-methyl-3-aza- 8-((1(2)H-tetrazole-5-thio)methyl)bicyclo[3.3.0]octane2-carboxylate, ethyl N-methoxycarbonyl-3-aza-8-((1(2)H-tetrazole- 5-thio)methyl)bicyclo [3.3.0]octane-2-carboxylate, 3-aza-8-(carboxymethyl)bicyclo[3.3.0]octane-2-carboxylic acid, ethyl 3-aza-8-(carboxymethyl)bicyclo[3.3.0]octane-2-carboxylate, N-acetyl -3-aza-8-( carboxymethyl)bicyclo[ 3.3.0] octane-2-carboxylic acid, and ethyl N-memhoxycarbonyl-3-aza- 8-( carboxymethyl)bicyclo[ 3.3.0]octane-2-carboxylate.

While all the formula VI compounds of the present invention are believed to be useful in the synthesis of the formula I compounds, certain compounds of the invention are preferred for such use. Preferably, $R^6$ is acyl, alkoxycarbonyl, or arylalkoxycarbonyl, and $R^4$ is $C_1$–$C_6$ alkyl, substituted alkyl, or arylalkyl. More preferably, $R^6$ is alkoxycarbonyl or arylalkoxycarbonyl, and $R^4$ is $C_1$–$C_6$ alkyl or arylalkyl. Most preferably, $R^6$ is an arylalkoxycarbonyl group and $R^4$ is a $C_1$–$C_6$ alkyl group. The most preferred formula VI compound for use in the synthesis of the formula I compounds is the compound wherein $R^6$ is benzyloxycarbonyl and $R^4$ is ethyl.

Similarly, while all the formula IX compounds of the present invention are believed to be useful in the synthesis of the formula I compounds, certain compounds of the invention are preferred for such use. Preferably, $R^6$ is acyl, alkoxycarbonyl, or arylalkoxycarbonyl, and $R^4$ is $C_1$–$C_6$ alkyl, substituted alkyl, or arylalkyl. More preferably, $R^6$ is alkoxycarbonyl or arylalkoxycarbonyl, and $R^4$ is $C_1$–$C_6$ alkyl or arylalkyl. Most preferably, $R^6$ is an arylalkoxycarbonyl group and $R^4$ is a $C_1$–$C_6$ alkyl group. The most preferred formula IX compound for use in the synthesis of the formula I compounds is the compound wherein $R^6$ is benzyloxycarbonyl and $R^4$ is ethyl.

The formula I compounds of the present invention have the relative stereochemistry shown below:

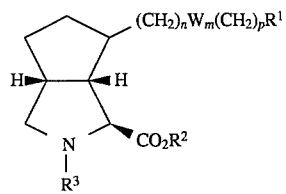

The compounds of the present invention possess at least four asymmetric carbon atoms. The asymmetric centers are the substituted carbon atom adjacent to the ring $NR^3$ group (2), the carbon atom where the group $(CH_2)_n W_m (CH_2)_p R^1$ is attached to the ring (8), and the two ring fusion carbon atoms (1 and 5). As such, the compounds can exist as diastereomers, as enantiomers, or as a racemic modification (racemate). The present invention includes each enantiomer or diastereomer, mixtures of enantiomers (including racemates), and mixtures of diastereomers. The configurations for the preferred diastereomers are 1S,2S,5R,8S and 1S,2S, 5R,8R. The preferred racemates are 1SR,2SR,5RS,8SR and 1SR,2SR,5RS,8RS. The most preferred racemate is 1SR, 2SR,5RS,8RS. The most preferred enantiomer is 1S,2S,5R, 8R. The relative and absolute stereochemistry for this most preferred enantiomer is shown in the following formula:

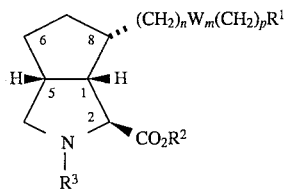

The enantiomers of the formula I compounds, as well as the enantiomers of the racemic intermediate compounds, are resolved using standard resolution techniques. See Jacques, Collet, and Wilen, Enantiomers, Racemates, and Resolutions, John Wiley and Sons, N.Y., 1981. The preferred method for the resolution of these enantiomers is the formation of diastereomeric salts between the racemic modifications and optically-active (chiral) resolving agents. See, Jacques, Collet, and Wilen, Chapter 5. The present compounds can be resolved using either acidic or basic chiral resolving agents. Examples of suitable acidic chiral resolving agents include (+)-camphoric acid, (−)-dibenzoyltartaric acid, diacetoneketogulonic acid, (+) and (−)-mandelic acid, (−)-malic acid, (+) and (−)-quinic acid, and (+) and (−)-tartaric acid. Examples of suitable basic chiral resolving agents include brucine, cinchonidine, cinchonine, strychnine, (+) and (−)-ephedrine, (−)-2-amino-1-butanol, (+) and (−)-α-methylbenzylamine, (+)-amphetamine, and (+)-deoxyephedrine.

The compounds of the present invention may contain a tetrazol-5-yl group, which is known to exist as tautomeric structures. The tetrazole, having the double bond on the nitrogen atom at the 1-position and the hydrogen on the nitrogen atom at the 2-position is named as a 2H tetrazole and is represented by the following structure.

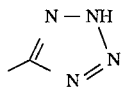

The corresponding tautomeric form wherein the hydrogen is at the nitrogen atom at the 1-position and the double bond on the nitrogen atom at the 4-position is named as a 1H-tetrazole. The 1H-tetrazole is represented by the following formula.

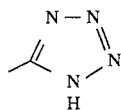

Mixtures of the two tautomers are referred to herein as 1(2)H-tetrazoles. The present invention contemplates both tautomeric forms as well as the combination of the two tautomers. Similarly, the tetrazole-5-thio (thiotetrazole) groups can exist as the 1-tetrazole-5-thio group or 2H-tetrazole- 5-thio group.

The present invention includes the pharmaceutically acceptable salts of the compounds defined by formula I. These salts can exist in conjunction with the acidic or basic portion of the molecule and can exist as acid addition, primary, secondary, tertiary, or quaternary ammonium, alkali metal, or alkaline earth metal salts. Generally, the acid addition salts are prepared by the reaction of an acid with a compound of formula I, wherein $R^3$ is hydrogen, $C_1$–$C_{10}$ alkyl, or arylalkyl. The alkali metal and alkaline earth metal salts are generally prepared by the reaction of the hydroxide form of the desired metal salt with a compound of formula I, wherein $R^2$ is hydrogen.

Acids commonly employed to form such salts include inorganic acids such as hydrochloric, hydrobromic, hydriodic, sulfuric, and phosphoric acid, as well as organic acids such as para-toluenesulfonic, methanesulfonic, oxalic, para-bromophenylsulfonic, carbonic, succinic, citric, benzoic, and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, meta-phosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, furmarate, hippurate, maleate, butyne-1,4-dioate, hexyne-1,6-dioate, benzoate, chlorobenzoate, methylbenzoate, dinitrobenzoate, hydroxybenzoate, methomybenzoate, phthalate, sulfonate, xylenesulfonate, phenylacetate, phenylpropionate, phenylbutyrate, citrate, lactate, α-hydroxybutyrate, glycolate, maleate, tartrate, methanesulfonate, propanesulfonate, naphthalene-1-sulfonate, napthalene-2-sulfonate, mandelate, ammonium, magnesium, tetramethylammonium, potassium, trimethylammonium, sodium, methylammonium, calcium, and the like salts.

The formula I compounds of the present invention are conveniently synthesized from the formula II compounds. The preferred formula II compound for use in the preparation of the formula I compounds is ethyl N-methoxycarbonyl-3-azabicyclo[3.3.0]octan-8-one-2-carboxylate (9). The synthesis of the formula II compounds is shown in Scheme I.

Scheme I

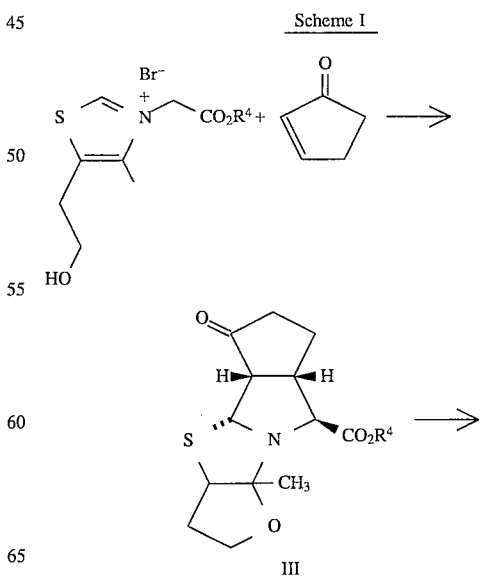

9
-continued
Scheme I

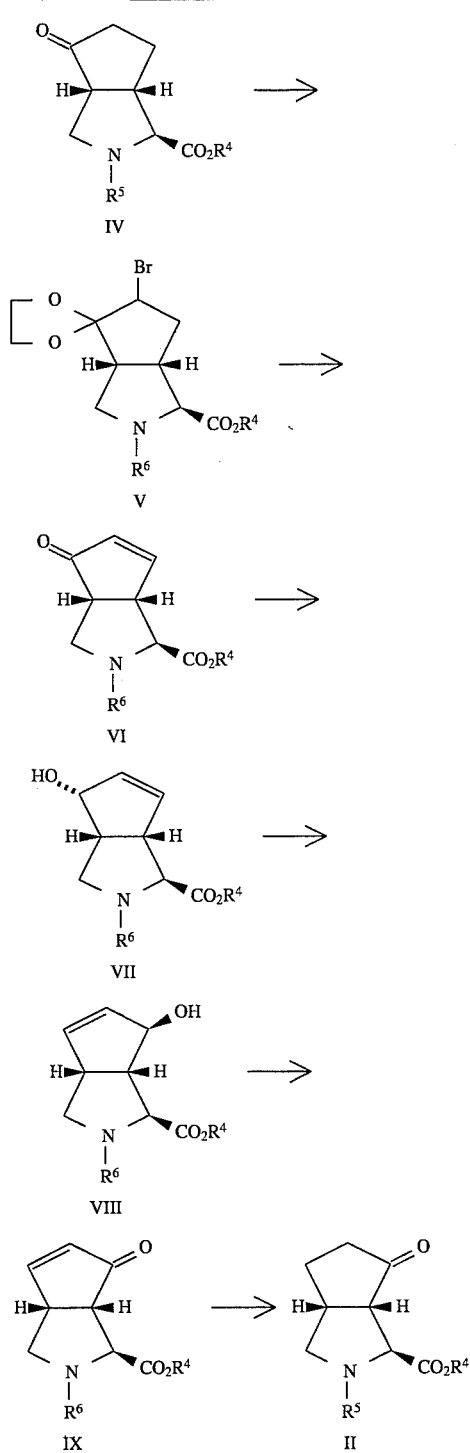

Generally, an azomethine ylid is reacted with cyclopentenone to produce cycloadduct III. This cycloadduct is reduced and hydrolyzed to prepare bicyclic intermediate IV. The keto group of intermediate IV is transposed from C-6 to C-8 by a series of chemical transformations to produce intermediate II. First, the C-7 position is oxidized to prepare bromo intermediate V. This intermediate is dehydrohalogenated to produce intermediate VI. The ketone function is reduced selectively producing intermediate VII, and rearranged to form intermediate VIII. Oxidation of this intermediate leads to intermediate IX, and selective reduction of the double bond produces a formula II compound.

Intermediate III, wherein $R^4$ is $C_1$–$C_6$ alkyl, substituted alkyl, cycloalkyl, or arylalkyl, is prepared by a 1,3-dipolar cyclo-addition reaction between an azomethine ylid and 2-cyclopentene-1-one. The preferred azomethine ylid for this reaction is 3-(ethoxycarbonylmethyl)-5-(2-hydroxyethyl)- 4-methylthiazolium bromide ($R^4$ is ethyl). This azomethine ylid is conveniently prepared as described in Preparation 1. Other azomethine ylids, wherein $R^4$ is alkyl, substituted alkyl, cycloalkyl, or arylalkyl, are prepared from the corresponding bromoacetic esters. The cycloaddition reaction is preferably carried out in a polar organic solvent, such as acetonitrile, and in the presence of a tertiary amine base. Suitable tertiary amine bases for this reaction include triethylamine, N,N,-diisopropylethylamine, 4-(dimethylamino)pyridine, and 1,8-diazabicyclo[5.4.0]undec-7-ene (DBU). The reaction is typically carried out at a temperature of about 10° C. to about 50° C., preferably at room temperature. The cycloaddition reaction is generally complete after about two hours.

Intermediate III, prepared by the above route, exists as a mixture of diastereomers. The diastereomers have the relative configurations as shown below:

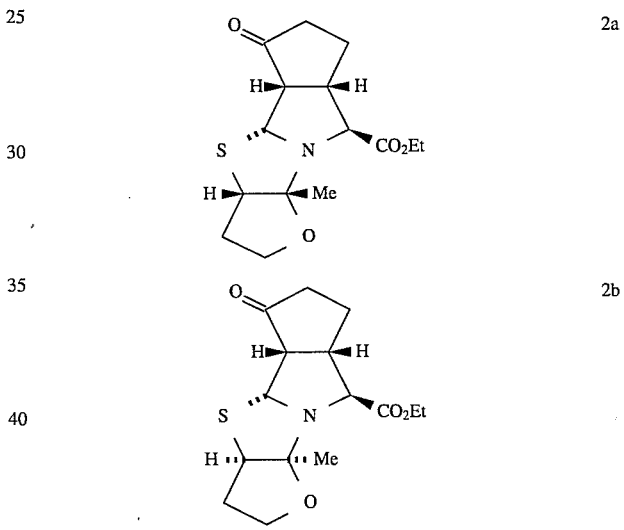

These diastereomers can be separated by preparative high pressure liquid chromatography; however, the mixture of diastereomers is preferably used in the synthesis of intermediate IV.

Intermediate IV, wherein $R^4$ is as defined above and $R^5$ is hydrogen, is prepared by reduction and hydrolysis of cycloadduct III. The first step is reduction of the sulfur-carbon bond to produce a hemiaminal. This reduction is typically carried out in an organic solvent, such as toluene or xylene, at the reflux temperature of the solvent. A suitable reducing agent is tributyltin hydride. The reaction is typically carried out with the addition of a radical initiator, such as 2,2'-azobisisobutylnitrile (AIBN). When the reaction is carried out in toluene, using tributyltin hydride as the reducing agent, the reduction is generally complete after about 6 hours.

The second step is hydrolysis of the reduced intermediate to produce intermediate IV. This hydrolysis is carried out in a polar organic solvent, such as ether, or a water miscible organic solvent, such as ethanol, in the presence of an acid, preferably a catalytic amount of acid. Suitable acids for this hydrolysis include hydrochloric acid, sulfuric acid, sodium bisulfate, p-toluenesulfonic acid, trifluoroacetic acid, methanesulfonic acid, and trifluoromethanesulfonic acid; the preferred acid is dilute hydrochloric acid. The reaction is typically carried out at a temperature of about 10° C. to about 50° C., preferably at room temperature. When the reaction is carried out using a two-phase mixture comprising dilute hydrochloric acid and ether, the reaction is typically complete after about 14 hours.

Intermediate IV, wherein $R^5$ is hydrogen, is preferably protected on the ring nitrogen for further synthetic transformations. Methods for the protection of amino groups are generally described in McOmie, Protective Groups in Organic Chemistry, Plenum Press, N.Y., 1973, and in Greene and Wuts, Protecting Groups in Organic Syntheeis, 2d, ed., John Wiley & Sons, N.Y., 1991. Suitable protecting groups are acyl, alkoxycarbonyl, aryloxycarbonyl, or an arylalkoxycarbonyl group. The preferred protecting groups are alkoxycarbonyl and arylalkoxycarbonyl groups. Most preferably, the protecting group is an arylalkoxycarbonyl group, such as benzyloxycarbonyl. The benzyloxycarbonyl protected intermediate IV is prepared by the reaction of the formula IV compound wherein $R^5$ is hydrogen with benzyl chloroformate. This reaction is carried out in a polar organic solvent, such as ethyl acetate, in the presence of a base. Suitable bases for this transformation include sodium hydroxide, triethylamine, N,N-diisopropylethylamine, potassium carbonate, and sodium bicarbonate; the preferred base is sodium hydroxide. The reaction is typically carried out at a temperature of about 5° C. to about room temperature, preferably at 5° C.

Intermediate V, wherein $R^4$ is as defined above and $R^6$ is acyl, alkoxycarbonyl, aryloxycarbonyl, or arylalkoxycarbonyl, is prepared by ketalization and oxidation of intermediate IV. These transformations are carried out in one step by reacting intermediate IV, wherein $R^5$ is acyl, alkoxycarbonyl, aryloxycarbonyl, or arylalkoxycarbonyl, with pyridinium bromide perbromide in ethylene glycol. This reaction is typically carried out at a temperature of about 50° C. to about 75° C., preferably at 60° C. This transformation is typically complete after about one hour.

Intermediate V is dehydrohalogenated and the ketal hydrolyzed to produce enone intermediate VI, wherein $R^4$ and $R^6$ are as defined previously. Intermediate V is dehydrohalogenated by reaction with an amine base, such as 1,8-diazabicyclo[5.4.0]undec-7-ene (DBU), pyridine, N,N-diisopropylethylamine, 4-(dimethylamino)pyridine, or triethylamine. The reaction is typically carried out at a temperature of about 60° C. to about 100° C., preferably at 85° C. After a period of about 18 hours, the reaction mixture may be diluted with acetone and sodium bisulfate for hydrolysis of the ketal. This hydrolysis is preferably carried out at room temperature and generally requires about three hours for completion.

Reduction of the ketone function of intermediate VI produces intermediate VII, wherein $R^4$ and $R^6$ are as defined above. This transformation is preferably carried out using a hydride reducing agent that selectively adds in a 1,2 manner to the the enone system. A suitable hydride reducing agent is the combination of cerium(III) chloride heptahydrate and sodium borohydride. This reduction is typically carried out in an organic solvent such as ethanol, at a temperature of about 0° C. to about room temperature, preferably at 5° C. This reduction is typically complete after about 18 hours.

Intermediate VII is used to produce its structural isomer, intermediate VIII. This transformation is affected by conversion of intermediate VII into the corresponding six substituted selenide by reaction with 2-nitrophenyl selenocyanae and tributylphosphine in the presence of pyridine. This transformation is typically carried out at a temperature of about −20° C. to about 20° C., preferably at a temperature of about −20° C. Suitable solvents for this reaction are polar organic solvents, such as tetrahydrofuran. The reaction may be carried out using pyridine as the solvent. Preferably, the pyridine is added about one hour after mixing the other reagents. The intermediate nitrophenyl selenide is then oxidized by the addition of an oxidizing agent, such as hydrogen peroxide, to the reaction mixture, causing a [2,3]-sigmatropic rearrangement to give intermediate VIII. Preferably, this oxidation is carried out using 30% hydrogen peroxide at room temperature. The oxidation and rearrangement are typically complete after about two hours.

Intermediate VIII is then oxidized to produce intermediate IX, wherein $R^4$ and $R^6$ are as defined previously. This oxidation is carried out by reacting intermediate VIII with an oxidizing agent. Suitable oxidizing agents include chromic acid based oxidants, such as Jones reagent, pyridinium dichromate, and pyridinium chlorochromate. The preferred oxidant for this transformation is pyridinium dichromate. The oxidation is typically carried out in an organic solvent, such as methylene chloride, at room temperature. The enone intermediate IX is conveniently isolated by filtering the reaction mixture through a filter agent, such as Celite, and is used without further purification.

This intermediate is reduced to produce intermediate II, wherein $R^4$ is as defined previously and $R^5$ is hydrogen, acyl, alkoxycarbonyl, aryloxycarbonyl, or arylalkoxycarbonyl. The preferred method of reduction is catalytic hydrogenation. Suitable catalysts for this transformation include platinum on carbon, palladium on carbon, platinum on aluminum oxide, and palladium on aluminum oxide. The preferred catalyst for the reduction is 5% palladium on carbon. The reduction is typically carried out in an organic solvent such as tetrahydrofuran at a hydrogen pressure of about 60 psi and at room temperature. This reduction is typically complete after about two hours. When $R^6$ is a benzyloxycarbonyl group, this protecting group is removed during the reduction.

The ring nitrogen is preferably protected for subsequent synthetic transformations. Suitable methods are described in McOmie and Greene and Wuts. Suitable protecting groups are acyl, alkoxycarbonyl, aryloxycarbonyl, and arylalkoxycarbonyl groups. The preferred protecting groups are alkoxycarbonyl and arylalkoxycarbonyl groups. For convenience, the nitrogen may be reprotected by the addition of carbonates, such as dimethyl pyrocarbonate, to the catalytic reduction reaction.

The compounds of the present invention are synthesized from the formula II compounds by a number of different routes. The specific synthetic steps of the routes described herein may be combined in other ways to prepare the formula I compounds. The following discussion is not intended to be limiting to the scope of the present invention, and should not be so construed. The synthesis of the formula I compounds, wherein n or p is 1 and m is 0, are prepared as shown in Scheme II.

Scheme II.

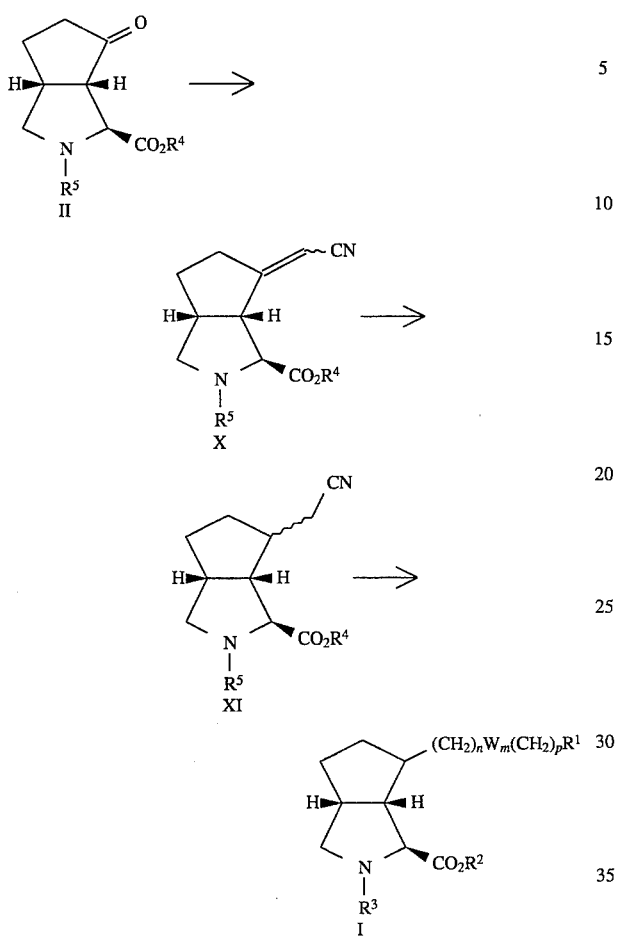

Intermediate II is reacted with a Wittig reagent or a Horner-Emmons reagent to produce the intermediate of general formula X. The use of a Horner-Emmons reagent of the general formula $(CH_3CH_2O)_2POCH_2CN$ is preferred. This reaction is generally accomplished by treating the diethylphosphonate with a strong base, such as sodium hydride, to generate the sodium salt of the phosphonate. This phosphonate salt is then reacted in a non-reactive solvent, such as tetrahydrofuran, with a formula II compound to provide intermediate X. This reaction is generally carried out between 0° C. and the reflux temperature of the solvent, preferably at room temperature.

Intermediate X is then reduced to provide the corresponding saturated analog. A preferred method of accomplishing this reduction is catalytic hydrogenation. Suitable catalysts for this transformation include palladium on carbon, platinum on carbon, and palladium on barium sulfate. The preferred catalyst is 5% palladium on barium sulfate. The reduction is carried out in an organic solvent, such as methanol, ethanol, ethyl acetate, or tetrahydrofuran.

The resulting intermediate XI is converted into a compound of this invention by conversion of the nitrile group to either a carboylic acid or a tetrazole. The nitrile group is converted into tetrazole by reaction with tributyltin azide. This reaction is conducted at a temperature of about 50° C. to about 120° C., preferably at about 85° C. to about 90° C., for about 48 hours to about 120 hours. The product of this reaction may be isolated, but is preferably hydrolyzed directly to a compound of the invention by acid or base hydrolysis. For example, the carboxy and nitrogen protecting groups are removed by mixing the product with 6N hydrochloric acid and heating to reflux for about 18 hours.

Alternatively, the corresponding carboxylic acid can be prepared from the same nitrile intermediate XI by heating the nitrile with acid, preferably at the reflux temperature of the solution. This reaction effectively hydrolyzes the nitrile to the acid and removes the $R^4$ and $R^5$ groups to provide the formula I compound wherein $R^2$ and $R^3$ are hydrogen. The preferred acid for this transformation is 6N hydrochloric acid.

The formula I compounds wherein n is 2 are prepared as shown in Scheme III.

Scheme III.

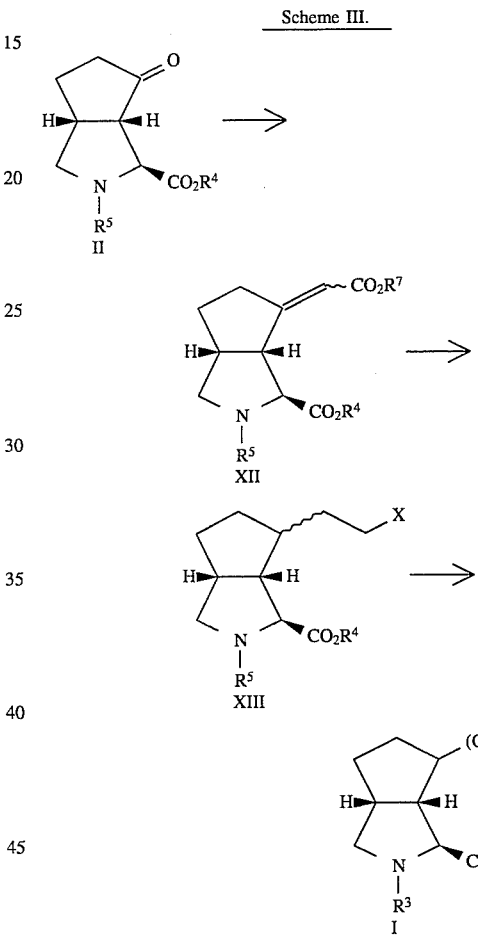

Intermediate II is reacted with a Horner-Emmons reagent of the general formula $(CH_3CH_2O)_2POCH_2CO_2R^7$, wherein $R^7$ is a carboxy protecting group (e.g. benzyl). This reaction is generally accomplished by treating the appropriate diethylphosphonate with a strong base, such as sodium hydride, to generate the sodium salt of the phosphonate. The phosphonate salt is then reacted in a non-reactive solvent, such as dry tetrahydrofuran, with the formula II compound to provide the unsaturated derivative of formula XII. This reaction is generally carried out at room temperature with a slight excess of the phosphonate salt.

Intermediate XII is then reduced to provide the corresponding saturated analog, a compound of general formula Xlll, wherein X is OH. The preferred method of accomplishing this reduction is a two-step process wherein the olefin is reduced by catalytic hydrogenation followed by reduction of the carboxlate group. Suitable catalysts include palladium on carbon, palladium on barium sulfate, platinum on carbon, and palladium on alumina; the preferred catalyst is 5% palladium on carbon. The reduction is typically carried out at room temperature and in an inert solvent, such as methanol, ethanol, ethyl acetate, or tetrahydrofuran.

The second step is reduction of the carboxylate group. suitable reducing agents include diborane and borane-methyl sulfide complex, preferably borane-methyl sulfide complex. The reduction is typically carried out in an organic solvent, such as tetrahydrofuran, at a temperature of about 0° C. to about 25° C.

The hydroxy intermediate XIII may be converted to bromo intermediate XIII, wherein X is Br. This compound is prepared by the reaction of the hydroxy intermediate with triphenylphosphine and bromine. A solution of triphenylphosphine in an organic solvent, such as methylene chloride, is treated with bromine to form the brominating agent, then a solution of the hydroxy intermediate in pyridine is added.

The bromo intermediate XIII is reacted with thiotetrazole to prepare the formula I compounds wherein $R^1$ is a thiotetrazole group. This reaction is typically carried out in the presence of an amine base in an organic solvent at a temperature of about 50° C. to 100° C. Suitable amine bases include triethylamine, N,N-diisopropylethylamine, pyridine, and N-methylmorpholine. Preferably, the amine base is N,N-diisopropylethylamine and the reaction is carried out in acetonitrile at a temperature of about 65° C. The protecting groups on the carboxylic acid and nitrogen functionalities may be removed subsequently by acid hydrolysis as described previously.

The bromo intermediate XIII is used to prepare the formula I compounds wherein m and p are 0, and $R^1$ is $PO_3H_2$. The bromo compound is converted to the corresponding diethyl phosphonate [X is $PO(OCH_2CH_3)_2$] by an Arbuzov reaction. Arbuzov, *Pure Appl. Chem.*, 9, 307–335(1964). The bromo compound is reacted with triethyl phophite to produce the corresponding diethyl phosphonate. The phosphate, carboxylate, and nitrogen protecting groups are removed by acid hydrolysis substantially as described above.

Alternatively, bromo intermediate XIII is used to prepare the formula I compounds wherein m and p are 0, and $R^1$ is $CO_2H$ or tetrazole. The bromo compound is first converted to corresponding nitrile (X is CN) by reaction with sodium cyanide. This transformation is carried out in a polar organic solvent, such as dimethyl sulfoxide, at a temperature off about 50° C. to about 65° C., preferably about 55° C. The nitrile intermediate is then converted into the corresponding carboxic acid or tetrazole as described above.

The bromo intermediate XIII is also used to prepare the formula I compounds wherein n is 2, W is S, m is 1, and p is 1. The bromo compound is reacted with a compound of the general formula $HSCH_2R^8$, wherein $R^8$ is CN, $CO_2CH_2CH_3$, tetrazole, or $PO(OCH_2CH_3)$. This reaction is typically carried out in the presence of an amine base, such as triethylamine or N,N-diisopropylethyamine, at a temperature of about 50° C. to about 100° C. The product of this reaction is converted to a formula I compound, wherein $R^2$ and $R^3$ are hydrogen, by acid hydrolysis substantially as described above.

Alternatively, the hydroxy intermediate XIII is used to prepare the formula I compounds of the invention wherein W is oxygen, m is 1, and p is 1. The hydroxyl group is first converted into a methoxyethoxymethyl group using standard synthetic methods. One such method is the reaction of hydroxy intermediate XIII with 2-methoxyethoxymethyl chloride in an organic solvent, such as methylene chloride, and in the presence of an amine base. The preferred amine base for use in this transformation is N,N-diisopropylethylamine. Preferably, the reaction is initially carried out at a temperature of 0° C. and allowed to warm slowly to room temperature.

This intermediate is then converted into a formula XIII compound wherein X is $OCH_2CN$. The methoxyethoxymethyl intermediate from above is reacted with trimethylsilyl cyanide in the presence of a Lewis acid, such as boron trifluoride etherate. This reaction is typically carried out in an organic solvent, such as methylene chloride, at a temperature of about 0° C. to about 5° C. The resulting nitrile intermediate is then used to prepare the corresponding carboxylic acid or tetrazole compounds using the procedures described above.

The formula I compounds wherein n is 0, W is S or O, and m is 1, are prepared as described in Scheme IV.

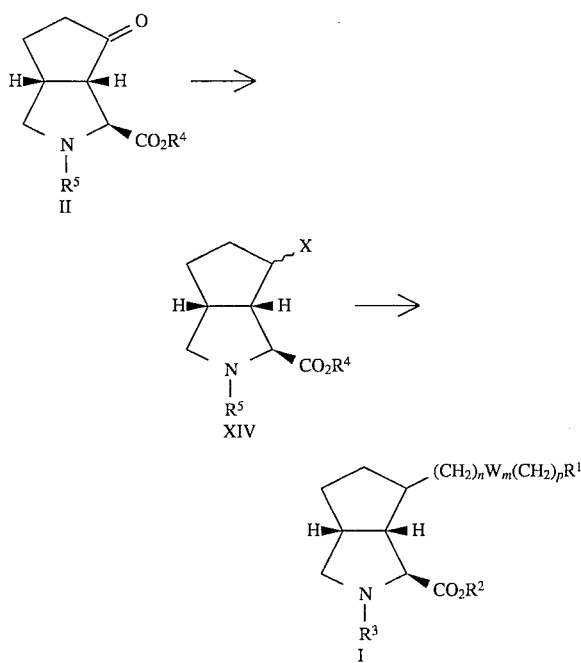

Scheme IV.

Intermediate II is reduced to prepare hydroxy intermediate XIV, wherein X is OH. This reduction is carried out using a hydride reducing agent, such as sodium borohydride or sodium cyanoborohydride, in an organic solvent, such as ethanol or isopropanol. The reaction is initially carried out at a temperature of about 0° C. and allowed to warm to room temperature. The hydroxy intermediate XIV can be converted into the corresponding methoxyethoxymethyl ether using the procedure substantially as described above and in the accompanying examples. This compound is then used for preparation of the formula I compounds wherein n is 0, W is O, m and p are 1, and $R^1$ is a carboxylic acid or a tetrazole group.

Alternatively, hydroxy intermediate XIV, wherein X is OH, is converted to the corresponding bromo intermediate (X is Br). This transformation is carried out as described previously using triphenylphosphine and bromine. Bromo intermediate XIV, wherein X is Br, is used to prepare the formula I compounds wherein n is 0, W is S, m is 1, and p is 1, by reaction with a compound of the general formula $HSCH_2R^8$ as described above.

The formula I compounds wherein n is 1 can be prepared in a stereoselective manner as shown in Scheme V.

Scheme V.

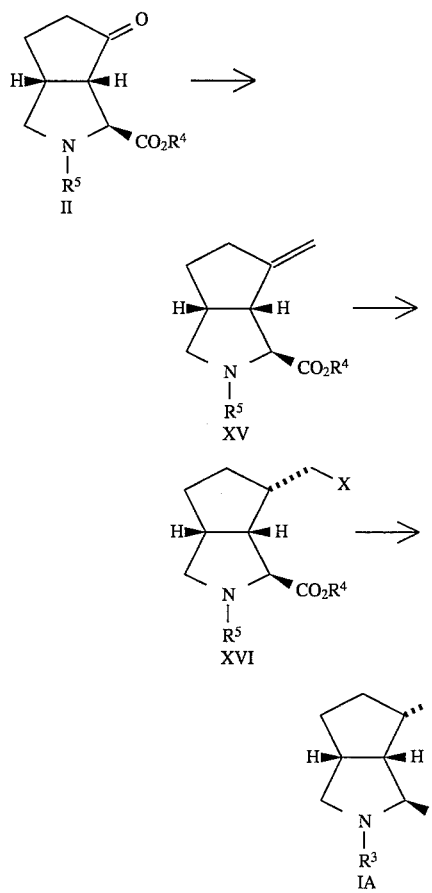

Scheme VI

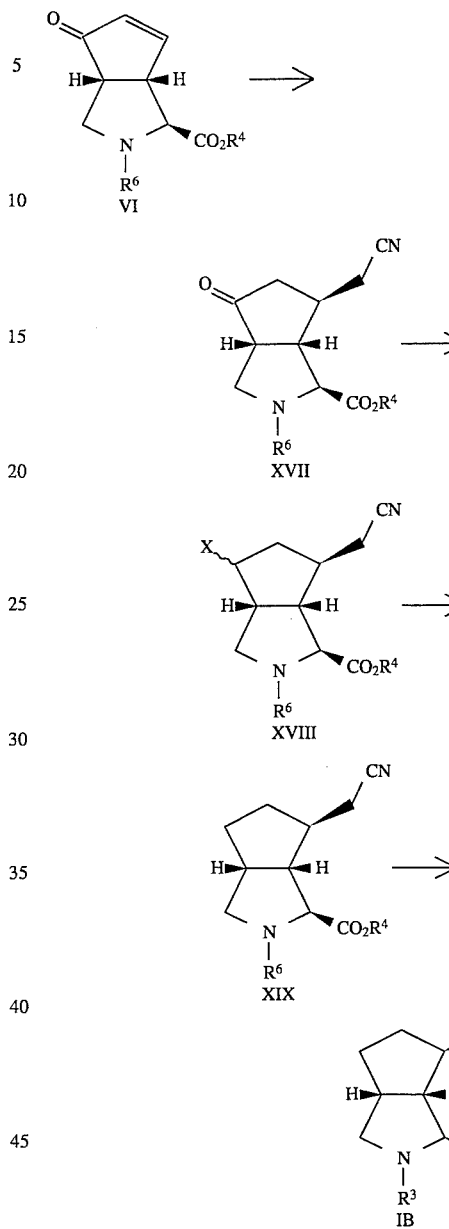

Intermediate II is reacted with a Wittig reagent to prepare the methylene derivative of formula XV. This reaction is generally accomplished by treating methyltriphenylphosphonium bromide with a strong base, such as sodium hydride or potassium bis(trimethylsilyl)amide, to generate the ylid. This ylid is reacted in a non-reactive solvent, such as tetrahydrofuran, with intermediate II to provide the methylene derivative of formula XV.

Intermediate XV is then stereoselectively converted to hydroxymethyl intermediate XVI, wherein X is OH. This transformation is accomplished by the reaction of intermediate XV with borane-methyl sulfide in an organic solvent, such as tetrahydrofuran. After about two hours at a temperature of about 0° C. to about 5° C., the reaction is treated with dilute aqueous base, such as 1 N sodium hydroxide, and with 30% hydrogen peroxide. After an additional hour at a temperature of about 5° C., the reaction is generally complete. This hydroxy intermediate is then used to prepare the formula I compounds substantially as described previously.

The formula I compounds of the opposite stereochemistry at C-8 can be stereoselectively prepared from enone intermediate VI as shown in Scheme VI.

Enone intermediate VI is first converted into a compound of formula XVII. This transformation is generally accomplished by treating trimethylsilylacetonitrile with a strong base, such as lithium bis(trimethylsilyl)amide, to generate the lithium salt, which is then reacted in a non-reactive solvent, such as tetrahydrofuran, with enone VI to provide the formula XVII compound.

Intermediate XVII is then converted to intermediate XIX by a series of synthetic transformations. First, the 6-keto group is reduced to hydroxy intermediate XVIII, wherein X is OH, by reaction with a hydride reducing agent, such as sodium borohydride or sodium cyanoborohydride. The hydroxy intermediate XVIII is then converted to the corresponding and bromo intermediate, wherein x is Br, using triphenylphosphine and bromine substantially as described previously. Bromo intermediate XVIII is next dehydrohalogenated by reaction with a strong amine base, such as 1,8-diazabicyclo[5.4.0]undec-7-ene (DBU). This transformation is typically carried out at a temperature of about 80° C. under a nitrogen atmosphere. The product of this reaction is then reduced to produce intermediate XIX. The preferred method of accomplishing this transformation is catalytic hydrogenation employing a suitable catalyst. Suitable catalysts for this transformation include palladium on carbon, platinum on carbon, palladium on barium sulfate, and palladium on alumina, preferably 5% palladium on barium sulfate. For convenience, this reduction is carried out in the presence of dimethylpyrocarbonate so that the product of the reaction has a methoxycarbonyl nitrogen protecting group. Cyanomethyl intermediate XIX is then converted to the formula I compounds using procedures substantially as described previously.

The formula I compounds wherein $R^3$ is acyl are prepared by the reaction of a formula I compound wherein $R^3$ is hydrogen with an activated ester of the desired acyl group. The term activated ester means an ester which renders the carboxyl function of the acylating group reactive to coupling with the amino group. The preferred activated ester is the 2,4,5-trichlorophenyl ester. The reaction is carried out in a polar organic solvent, such as dimethylformamide or tetrahydrofuran, at a temperature of about 25° C. to 110° C. for a period of about one to about five hours. The reaction for the formation of acyl derivatives of the formula I compounds is preferably carried out at a temperature of about 30° C. to about 70° C. for a period of about two to about four hours.

The formula I compounds wherein $R^3$ is a $C_1$–$C_{10}$ alkyl or arylalkyl group are prepared using standard synthetic methods. One method for the synthesis of these compounds is the reaction of the aldehyde corresponding to the $C_1$–$C_{10}$ alkyl or arylalkyl group with a formula I compound wherein $R^3$ is hydrogen in the presence of a reducing agent. Suitable reducing agents include sodium cyanoborohydride and formic acid. This reaction is typically carried out in a polar organic solvent, such as methanol or ethyl acetate, at room temperature. The formula I compounds wherein $R^3$ is alkoxycarbonyl, arylalkoxycarbonyl, or aryloxycarbonyl are prepared using procedures as described above for the synthesis of intermediates II and IV.

The formula I compounds wherein $R^2$ is $C_1$–$C_6$ alkyl, substituted alkyl, cycloalkyl, or arylalkyl are prepared from the corresponding compounds wherein $R^2$ is hydrogen. These compounds are generally prepared using standard synthetic methodologies. In a typical example, the formula I compound, wherein $R^2$ is hydrogen, is reacted with a substituted alkyl, cycloalkyl, or arylalkyl alcohol in the presence of acid to produce the corresponding mono or diester. Typically, this reaction is carried out with an excess of the alcohol in the presence of concentrated sulfuric acid.

The formula I compounds of the present invention are excitatory amino acid antagonists. In particular, these compounds are antagonists of the NMDA subtype of excitatory amino acid receptors. Therefore, another aspect of the present invention is a method of blocking the NMDA excitatory amino acid receptors in mammals which comprises administering to a mammal requiring decreased excitatory amino acid neurotransmission a pharmaceutically-effective amount of a compound of formula I.

The term "pharmaceutically-effective amount" is used herein to represent an amount of the compound of the invention which is capable of blocking the NMDA excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular, or intranasal routes. Alternatively, the compounds may be administered by continuous infusion. A typical daily dose will contain from about 0.01 mg/kg to about 30 mg/kg of the active compound of this invention. Preferred daily doses will be about 0.05 mg/kg to about 24 mg/kg, more preferably about 0.1 to about 20 mg/kg.

A variety of physiological functions have been shown to be subject to influence by excessive or inappropriate stimulation of excitatory amino acid neurotransmission. The formula I compounds of the present invention are believed to have the ability to treat a variety of neurological disorders in mammals associated with this condition, which include acute neurological disorders such as cerebral deficits subsequent to cardiac bypass surgery and grafting, stroke, cerebral ischemia, spinal cord trauma, head trauma, perinatal hypoxia, cardiac arrest and hypoglycemic neuronal damage. The formula I compounds are believed to have the ability to treat a variety of chronic neurological disorders such as Alzheimer's Disease, Huntington's Chorea, amyotrophic lateral sclerosis, AIDS-induced dementia, ocular damage and retinopathy, and idiopathic and drug-induced Parkinson's Disease. The present invention also provides methods for treating these disorders which comprise administering to a patient in need thereof an effective amount of a compound of formula I.

The formula I compounds of the present invention are also believed to have the ability to treat a variety of other neurological disorders in mammals that are associated with glutamate dysfunction, including muscular spasms, convulsions, migraine headaches, urinary incontinence, psychosis, opiate tolerance and withdrawal, anxiety, emesis, brain edema, chronic pain, and tardive dyskinesia. The formula I compounds are also useful as analgesic agents. Therefore, the present invention also provides methods for treating these disorders which comprise administering to a patient in need thereof an effective amount of a compound of formula I.

Experiments were performed to demonstrate the inhibitory activity of the formula I compounds of this invention at the N-methyl-D-aspartate (NMIDA) subtype of excitatory amino acid receptor. The formula I compounds were tested for their ability to inhibit NMDA receptor binding to rat membranes in a radioligand binding assay using [$^3$H] CGS19755. For these radioligand binding assays, male Sprague-Dawley rats were used. Displacement of the specific binding [$^3$H]CGS19755 (10 nM) to Triton-X-treated synaptosomal membranes of rat forebrain was used to determine NMDA receptor affinity. Non-specific binding was determined using 10 μM L-glutamate. Samples were incubated in an ice-bath for 30 minutes, and bound ligand was separated from the free ligand by rapid filtration through WHATMAN GF/B glass fiber filters. Murphy et al, *British J. Pharmacol.*, 95, 932–938(1988). The concentration of the formula I compound that inhibited 50% binding ($IC_{50}$, mean±standard error, n=3) was calculated by linear regression of displacement data transformed to the Hill equation as described by Bennett. Bennett, Neurotransmitter Receptor Binding, 57–90(1978). The results of the [$^3$H]CGS19755 binding assays are shown in Table I.

The formula I compounds were also tested for their ability to inhibit NMDA receptor binding using [$^3$H]MK-801 (New England Nuclear, Boston, Mass.). Rat brain cortices were extensively washed to remove endogenous glutamate and glycine. Cortices were homogenized in 20 volumes of ice-cold 0.32M sucrose and centrifuged at 1,000 xg for ten minutes. The supernatant was then centrifuged at 20,000 xg for 20 minutes. The resulting pellet was resuspended in 30 volumes of distilled water and centrifuged at 8,000 xg for 20 minutes. The resulting supernatant was centrifuged at 45,000 xg for 20 minutes and the pellet frozen in liquid nitrogen for at least 24 hours. On the day of the assay, the pellet was thawed at room temperature and resuspended in 30 volumes of ice-cold distilled water and centrifuged at 45,000 xg for 20 minutes. The final pellet was resuspended in 50 mM Tris (pH 7.4) at a concentration of 10 vol/gram wet weight of tissue.

The binding of [$^3$H]MK-801 to well washed rat cortical membranes was conducted in the presence of added glutamate (0.001 µM) and glycine (10 µM). Antagonists were incubated with [$^3$H]MK-801(2.5 nM) and membrane aliquots (µg/ml protein) in a final volume of 1 ml at 27° C. for two hours. Nonspecific [$^3$H]MK-801 binding was determined in the presence of 100 µM MK-801. Assays were terminated by filtering the samples over Whatman GF/B glass-fiber filters, presoaked in 0.05% polyethyleneimine, followed by a 10 ml ice cold saline wash.

These assays were performed in triplicate, and the mean values of three separate experiments were used to obtain the half maximal effective concentration. Final protein concentrations (0.5 mg/ml) for each assay were determined using the Lowry et al. (1951) method. Lowry, Rosebrough, Farr, and Randall, *J. Biol. Chem.*, 193, 265–275(1951). Analysis of the data was performed using a four-parameter logistic equation (Graphpad Software San Diego, Calif.).

TABLE 1

Receptor Binding of Formula I Compounds

| Compound No. | IC$_{50}$ (µM) | |
|---|---|---|
| | [$^3$H]-CGS19755 | [$^3$H]MK-801 |
| 12 | 0.73 ± 0.19 | 49.7 ± 14.2 |
| 13 | 1.19 ± 0.54 | 39.0 ± 8.7 |
| 22 | 26.1 ± 6.13 | >100 |
| 21 | 4.50 ± 0.98 | 37.7 ± 9.3 |
| 20 | 1.44 ± 0.04 | 47.3 ± 21 |
| 23 | >100 | >100 |
| 27 | 5.66 ± 0.15 | >100 |
| 32 | 1.31 ± 0.48 | 27.8 ± 12.2 |
| 33 | 0.67 ± 0.20 | 36.6 ± 7.0 |
| 38 | 3.13 ± 0.58 | 47.3 ± 7.62 |

The depolarization of rat cortical wedges was used to test the selectivity and potency of the formula I compounds as NMDA antagonist using a technique similar to that described by Harrison and Simmonds. Harrison and Simmonds, *Bri. J. Pharmacol.*, 84, 381–391(1984). Generally, 4-ml aliquots of NMDA (40 µM) were superfused (2 ml/min) on the gray matter at intervals of 15 to 20 minutes until stable responses where obtained. The tissue was then exposed for 15 minutes to various concentrations of the formula I compounds before retesting the agonist. The IC$_{50}$ values were calculated from linear regression of log dose-response curves, each point the mean of at least three observations on separate slices from more than one animal. The results of these tests are shown in Table II.

TABLE II

Antagonism of Cortical Wedge Depolarization by Formula I Compounds

| Compound No. | IC$_{50}$ (µM) |
|---|---|
| 12 | 9.5 ± 5 |
| 13 | 52 ± 8 |
| 22 | — |
| 21 | >100 |
| 20 | >100 |
| 23 | >100 |
| 27 | — |
| 32 | 59.7 ± 10.01 |
| 33 | 28.6 ± 5.6 |
| 38 | >100 |

The data shows that the formula I compounds possess affinity for the NMDA ionotropic glutamate receptors. The formula I compounds, in particular compounds 12 and 33 displaced [$^3$H]CGS19755 with IC$_{50}$ values less than 1 µM (Table I). The cortical wedge assay distinguishes between agonist and antagonist activity. The formula I compounds, in particular compounds 12 and 33, are shown to be NMDA receptor antagonists (Table II).

The compounds of the present invention are preferably formulated prior to administration. Therefore, another aspect of the present invention is a pharmaceutical formulation comprising a compound of formula I and a pharmaceutically-acceptable carrier, diluent, or excipient.

The present pharmaceutical formulations are prepared by known procedures using well-known and readily available ingredients. In making the compositions of the present invention, the active ingredient will usually be mixed with a carrier, or diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of the active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. compositions of the inventions may be formulated so as to provide quick, sustained, or delayed release of the active ingredient after administration to the patient by employing procedures well known in the art.

The compositions are preferably formulated in a unit dosage form, each dosage containing from about 5 mg to about 5000 mg, more preferably about 25 mg to about 3000 mg of the active ingredient. The most preferred unit dosage form contains about 100 mg to about 2000 mg of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| 3-Aza-8-((1(2)H-tetrazol-5-yl)methyl)-bicyclo[3.3.0]octane-2-carboxylic Acid | 250 |
| Starch, dried | 200 |
| Magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/tablet) |
| --- | --- |
| 3-Aza-8-(carboxymethyl)bicyclo-[3.3.0]octane-2-carboxylic Acid | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight % |
| --- | --- |
| 3-Aza-(2-carboxyethyl)bicyclo-[3.3.0]octane-2-carboxylic Acid | 0.25 |
| Ethanol | 29.75 |
| Propellant 22 | 70.00 |
| (chlorodifluoromethane) |  |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4

Tablets each containing 60 mg of active ingredient are made as follows:

| 3-Aza-8-((1(2)H-tetrazol-5-thio)methyl)bicyclo[3.3.0]-octane-2-carboxylic Acid | 60 mg |
| --- | --- |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg medicament are made as follows:

| 3-Aza-8-((1(2)H-tetrazol-5-yl)methyl)-bicyclo[3.3.0]3-carboxylic acid | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 sieve, and filled into hard gelatin capsules in 200 mg quantities.

Formulation 6

Suppositories each containing 225 mg of active ingredient may be made as follows:

| 3-Aza-8-(carboxymethyl)bicyclo-[3.3.0]octane-2-carboxylic Acid | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| 3-Aza-(2-carboxyethyl)bicyclo-[3.3.0]octane-2-carboxylic Acid | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |

-continued

| | |
|---|---|
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| 3-Aza-8-((1(2)H-tetrazol-5-thio)methyl)bicyclo[3.3.0]-octane-2-carboxylic Acid | 100 mg |
| Mannitol | 100 mg |
| 5 N Sodium hydroxide | 200 μl |
| Purified water to total | 5 ml |

The following Examples further illustrate the compounds of the present invention and the methods for their synthesis. The Examples are not intended to be limiting to the scope of the invention in any respect, and should not be so construed. All solvents and reagents were used as obtained. Proton nuclear magnetic resonance ($^1$H NMR) spectra were obtained on a GE QE-300 spectrometer at 300.15 MHz or a Bruker AM-500 spectrometer at 500 MHz. Field description mass spectroscopy (FDMS) was performed using either a VG 70SE or a Varian MAT 731 instrument. The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection [plates dipped in a ceric ammonium molybdate solution (75 g of ammonium molybdate and 4 g of cerium (IV) sulfate in 500 mL of 10% aqueous sulfuric acid) and then heated on a hot plate]. Preparative high pressure liquid chromatography (preparative HPLC) was performed on a WATER'S PREP LC/500 instrument using silica-gel PREP Pak™ cartridges. Preparative centrifugal thin-layer chromatography (PC-TLC) was performed on a Harrison Model 7924A CHROMATOTRON using Analtech silica-gel GF rotors. Elemental analyses for carbon, hydrogen, and nitrogen were determined on a Control Equipment Corporation 440 Elemental Analyzer. Melting points were determined in open glass capillaries on a Thomas Hoover melting point apparatus, and are uncorrected.

Preparation 1

Preparation of 3-(Ethoxycarbonylmethyl)-5-(2-hydroxyethyl)-4-methylthiazolium Bromide (1)

A solution of 5-(2-hydroxyethyl)-4-methylthiazole (306 g) and ethyl bromoacetate (356.2 g) in ethanol (1 L) was heated to reflux. After two hours, the ethanol was removed by distillation and the residue treated with isopropanol (1.5 L). The resulting solution was cooled to about 0° C., causing crystallization of compound 1. After three hours, the crystalline material was separated from the mother liquor. Additional crystals were obtained by prolonged cooling of the mother liquor at 0° C. Combination of the crystalline material gave 474.3 g of compound 1. Melting point 96°–98° C.

Mass spectrum (FDMS): m/z=230 (M+–Br).

Analysis calculated for $C_{10}H_{16}BrNO_3S$: C, 38.72; H, 5.20; N, 4.52. Found: C, 38.64; H, 5.04; N, 4.47.

Preparation 2

Preparation of Compounds 2a and 2b

A mixture of the compound from Preparation 1(20 g) and 2-cyclopenten-1-one (25.0 g) in acetonitrile (30 ml) was treated with triethylamine (7.17 g). The resulting mixture was stirred at room temperature under a nitrogen atmosphere. After 24 hours, the reaction mixture was diluted with ether (200 ml) and brine (200 ml). The phases were separated and the aqueous phase was extracted with ether (3×200 ml). The organic phases were combined, washed with brine (200 ml), dried over potassium carbonate, and concentrated in vacuo to a dark oil. This oil was purified by preparative HPLC, eluting with a linear gradient of hexane/ethyl acetate (4:1) to hexane/ethyl acetate (1:1), to give two diastereomeric products. The first diastereomeric compound 2a (13.6 g), and the second diastereomeric compound 2b (1.98 g), were combined for use in the next step.

Compound 2a.
  Melting point 70°–74° C.
  Mass spectrum (FDMS): m/z=311 (M+).
  Analysis calculated for $C_{15}H_{21}NO_4S$: C, 57.86; H, 6.80; N, 4.50. Found: C, 57.63; H, 6.87; N, 4.29.

Compound 2b.
  Melting point 126°–128° C.
  Mass spectrum (FDMS): m/z=311 (M+).
  Analysis calculated for $C_{15}H_{21}NO_4S$: C, 57.86; H, 6.80; N, 4.50. Found: C, 57.56; H, 6.86; N, 4.33.

Preparation 3

Preparation of (1SR,2SR,5RS)-Ethyl N-Benzyloxycarbonyl-3-azabicyclo[3.3.0]octan-6-one-2-carboxylate (3)

A solution of the diastereomeric compounds prepared as described in Preparation 2(311 g), 2,2'-azobisisobutylnitrile (24.6 g), and tributyltin hydride (360 ml) in toluene (1.6 L) was heated to reflux under a nitrogen atmosphere. After six hours, the volatiles were removed by distillation. The residue was treated with ether (1 L) and 1N hydrochloric acid (1.1 L), and the resulting two-phase mixture vigorously stirred at room temperature. After 14 hours, the organic phase was removed, and the aqueous phase extracted with ether (10×1 L). The aqueous phase was then cooled to 5° C. and sequentially treated with ethyl acetate (1 L) and benzyl chloroformate (190 g). The resulting solution was vigorously stirred and treated with 50% sodium hydroxide (170 ml). After the addition of sodium hydroxide was complete, the reaction mixture was allowed to warm to room temperature. After one hour at room temperature, the organic phase was removed and the aqueous phase extracted with ethyl acetate (4×1 L). The combined organic phase was washed with water (1 L), dried over magnesium sulfate, and concentrated in vacuo to a red oil. This oil was purified by preparative HPLC, eluting with a linear gradient of hexane/ethyl acetate (4:1) to hexane/ethyl acetate (1:1), to give 212.8 g of compound 3 as a white solid. Melting 66°–68° C.

Mass spectrum (FDMS): m/z=331 (M+).

Analysis calculated for $C_{18}H_{21}NO_5$: C, 65.24; H, 6.39; N, 4.23. Found: C, 64.95; H, 6.39; N, 4.27.

EXAMPLE 1

Preparation of (1SR,2SR,5RS,7SR)-Ethyl N-Benzyloxycarbonyl-3-aza-6-ethylenedioxy-7-bromobicyclo[3.3.0]octan-2-carboxylate and (1SR,2SR,5RS,7RS)-Ethyl N-Benzyloxycarbonyl-3-aza-6-ethylenedioxy-7-bromobicyclo[3.3.0]octan-2-carboxylate (4)

A mixture of the compound prepared as described in Preparation 3(100 g) and pyridinium bromide perbromide (107.8 g) in ethylene glycol (200 ml) was warmed with stirring to about 60° C. After one hour, this mixture was poured into water, and the title compounds extracted with diethyl ether. The organic extracts were dried over magnesium sulfate and concentrated in vacuo. The residue was purified by preparative HPLC, eluting with a linear gradient of hexane to hexane/ethyl acetate (3:2), to give 88.8 g of the title compounds as a mixture of diastereomers.

Mass spectrum (FDMS): m/z=453, 455 (M+).

Analysis calculated for $C_{20}H_{24}NO_6Br$: C, 52.88; H, 5.33; N, 3.08. Found: C, 52.65; H, 5.46; N, 3.01.

EXAMPLE 2

Preparation of (1SR,2SR,5RS)-Ethyl N-Benzyloxycarbonyl-3-azabicyclo[3.3.0]oct-7-ene-6-one-2-carboxylate (5)

A mixture of the compound prepared as described in Example 1 (143.4 g) and 1,8-diazabicylo[5.4.0]undec-7-ene(96.1 g) was warmed to about 85° C. After about 18 hours, the reaction mixture was allowed to cool to room temperature. This mixture was treated with acetone (400 ml) and sodium bisulfate monohydrate (173.9 g), and the resulting mixture stirred at room temperature. After 3 hours, this mixture was diluted with water and the title compound extracted with diethyl ether. The ether extracts were dried over magnesium sulfate and concentrated in vacuo. The residue was purified by preparative HPLC, eluting with a linear gradient of hexane/ethyl acetate (9:1) to hexane/ethyl acetate (1:1), to give 84.6 g of compound 5.

Mass spectrum (FDMS): m/z=330 (M+H).

Analysis calculated for $C_{18}H_{19}NO_5$: C, 65.64; H, 5.81; N, 4.25. Found: C, 65.90; H, 5.94; N, 4.11.

EXAMPLE 3

Preparation of (1SR,2SR,5RS,6RS)-Ethyl N-Benzyloxycarbonyl-3-azabicyclo[3.3.0]oct-7-ene-6-ol-2-carboxylate (6)

A solution of the compound prepared as described in Example 2 (16.5 g) and cerium(III) chloride heptahydrate (18.7 g) in ethanol (500 ml) was cooled to about 5° C. and treated with sodium borohydride (1.9 g). After the addition of the sodium borohydride, the reaction mixture was allowed to warm to room temperature. After 18 hours, the reaction mixture was poured slowly into 1N hydrochloric acid (300 ml). The title compound was extracted with diethyl ether. The diethyl ether extracts were dried over magnesium sulfate and concentrated in vacuo. The residue was purified by preparative HPLC, eluting with a linear gradient of hexane/ethyl acetate (9:1) to hexane/ethyl acetate (1:1), to give 12.5 g of compound 6.

Mass spectrum (FDMS): m/z=332 (M+H).

Analysis calculated for $C_{18}H_{21}NO_5$: C, 65.24; H, 6.39; N, 4.23. Found: C, 65.52; H, 6.55; N, 4.52.

EXAMPLE 4

Preparation of (1SR,2SR,5RS,8SR)-Ethyl N-Benzyloxycarbonyl-3-azabicyclo[3.3.0]oct-6-ene-8-ol-2-carboxylate (7)

A solution of the compound prepared as described in Example 3 (6.89 g) and 2-nitrophenyl selenocyanate (4.72 g) in tetrahydrofuran (100 ml) was cooled to about −20° C. under a nitrogen atmosphere. The cooled solution was treated with tributylphosphine (5.2 ml) in one portion. After one hour, the reaction solution was treated with pyridine (100 ml) and the resulting mixture allowed to warm to room temperature. The reaction was then treated with 30% hydrogen peroxide (35 ml). After an additional two hours, the reaction mixture was added to 1N hydrochloric acid (200 ml), and the title compound was extracted with diethyl ember. The diethyl ether extracts were dried over magnesium sulfate and concentrated in vacuo. The residue was purified by preparative HPLC, eluting with a linear gradient of hexane to hexane/ethyl acetate (1:1), to give 4.97 g of compound 7.

Mass spectrum (FDMS): m/z=331 (M+).

Analysis calculated for $C_{18}H_{21}NO_5$: C, 65.24; H, 6.39; N, 4.23. Found: C, 65.06; H, 6.38; N, 3.98.

EXAMPLE 5

Preparation of (1SR,2SR,5RS)-Ethyl N-Benzyloxycarbonyl-3-azabicyclo[3.3.0]oct-6-ene-8-one-2-carboxylate (8)

A solution of the compound prepared as described in Example 4 (4.95 g) in methylene chloride (100 ml) was treated with pyridinium dichromate (6.9 g) and the resulting mixture was stirred at room temperature under a nitrogen atmosphere. After 14 hours, the reaction mixture was diluted with diethyl ether (300 ml) and the resulting mixture was filtered through CELITE. The filtrate was washed with 1N hydrochloric acid, dried over magnesium sulfate, and concentrated in vacuo to give 4.72 g of compound 8.

Mass spectrum (FDMS): m/z=329 (M+).

Analysis calculated for $C_{18}H_{19}NO_5$: C, 65.64; H, 5.81; N, 4.25. Found: C, 65.36; H, 5.62; N, 4.12.

EXAMPLE 6

Preparation of (1SR,2SR,5RS)-Ethyl N-Methoxycarbonyl-3-azabicyclo[3.3.0]octan-8-one-2-carboxylate (9)

A mixture of the compound prepared as described in Example 5 (4.70 g), dimethyl pyrocarbonate (3.83 g), and 5% palladium/carbon (1.0 g) in tetrahydrofuran (100 ml) was hydrogenated at a hydrogen pressure of 60 psi and at room temperature. After two hours, the catalyst was removed by filtration and the filtrate concentrated in vacuo to give 3.41 g of compound 9.

Mass spectrum (FDMS): m/z=255 (M+).

Analysis calculated for $C_{12}H_{17}NO_5$: C, 56.46; H, 6.71; N, 5.49. Found: C, 56.60; H, 6.83; N, 5.54.

EXAMPLE 7

Preparation of (E,Z)-(1SR,2RS,5SR)-Ethyl N-Methoxycarbonyl-8-cyanomethylene-3-azabicyclo [3.3.0]octane-2-carboxylate (10)

A mixture of sodium hydride (1.20 g, 60% dispersion in mineral oil) in tetrahydrofuran (100 ml) was treated with diethyl cyanomethylphosphonate (7.23 g). The resulting solution was stirred at room temperature under a nitrogen atmosphere for 15 minutes, and treated with a solution of the compound prepared as described in Example 6 (5.11 g) in tetrahydrofuran (50 ml). After an additional 30 minutes, the reaction mixture was carefully added to 1N hydrochloric acid. The title compound was extracted with diethyl ether, and the ether abstracts dried over magnesium sulfate and concentrated in vacuo. The title compound was purified by preparative HPLC, eluting with a linear gradient of ethyl acetate/hexanes (1:9) to ethyl acetate/hexane (1:1), to give 5.40 g of compound 10 as a mixture of diastereomers.

Mass spectrum (FDMS): m/z=278 ($M^+$)

Analysis calculated for $C_{14}H_{18}N_2O_4$: C, 60.42; H, 6.52; N, 10.07. Found: C, 60.42; H, 6.57; N, 10.05.

EXAMPLE 8

(1SR,2SR,5RS,8SR)-Ethyl N-Methoxycarbonyl-3-aza-8-(cyanomethyl)bicyclo [3.3.0]octane-2-carboxylate and (1SR,2SR,5RS,8RS)-Ethyl N-Methoxycarbonyl-3-aza-8-(cyanomethyl)bicyclo [3.3.0]octane-2-carboxylate (11)

A mixture of the compound prepared as described in Example 7 (4.1 g) and 5% palladium on barium sulfate (.83 g) in ethanol (95 mL) was hydrogenated under a hydrogen pressure of 60 psi and at room temperature. After two hours, the catalyst was removed by filtration, and the filtrate concentrated in vacuo to give 4.08 g of compound 11 as a mixture of distereomers.

Mass spectrum (FDMS): m/z=280 (M+).

Analysis calculated for $C_{14}H_{20}N_2O_4$: C, 59.99; H, 7.19; N, 9.99. Found: C, 59.90; H, 7.22; N, 9.86.

EXAMPLE 9

Preparation of (1SR,2SR,5RS,8SR)-3-Aza-8-((1 (2)H-tetrazol-5-yl)methyl)bicyclo[3.3.0]octane-2-carboxylic Acid and (1SR,2SR,5RS,8RS)-3-Aza-8-((1(2)H-tetrazol-5-yl) methyl)bicyclo[3.3.0]octane-2-carboxylic Acid (12)

A mixture of the compound prepared as described in Example 8 (1.11 g) and tributyltin azide (2.58 g) was heated to about 85° C.–90° C. under a nitrogen atmosphere. After 72 hours, the mixture was treated with 6N hydrochloric acid (10 ml), and the resulting mixture heated to reflux. After an additional 18 hours, the reaction mixture was allowed to cool to room temperature, extracted with diethyl ether, and the combined ether extracts concentrated to dryness. The title compound was purified by cation exchange chromatography (DOWEX 50 X8-100), eluting with 5% pyridine/water. The fractions containing the title compound were evaporated to dryness and the residue crystalized from ethanol/water to give 0.81 g of compound 12 as a mixture of diastereomers.

Mass spectrum (FDMS): m/z=238 (M+H).

Analysis calculated for $C_{10}H_{15}N_5O_2$: C, 50.62; H, 6.37; N, 29.52. Found: C, 50.90; H, 6.39; N, 29.26.

EXAMPLE 10

Preparation of (1SR,2SR,5RS,8SR)-3-Aza-8-(carboxymethyl)bicyclo [3.3.0]octane-2-carboxylic Acid and (1SR,2SR,5RS,8RS)-3-Aza-8-(carboxymethyl)bicyclo [3.3.0]octane-2-carboxylic Acid (13)

A mixture of the compound prepared as described in Example 8 (.78 g) and 6N hydrochloric acid (25 ml) was heated to reflux. After 50 hours, the reaction mixture was concentrated to dryness under reduced pressure. The title compound was purified by cation exchange chromatography (DOWEX 50 X8-100), eluting with 5% pyridine/water. The fractions containing the title compound were combined and concentrated in vacuo, and the residue crystallized from ethanol/water to give 0.44 g of compound 13 as a mixture of diastereomers.

Mass spectrum (FDMS): m/z=214 (M+H).

Analysis calculated for $C_{10}H_{15}NO_4$: C, 56.33; H, 7.09; N, 6.57. Found: C, 56.53; H, 7.33; N, 6.78.

EXAMPLE 11

Preparation of (E,Z)-(1SR,2RS,5SR)-Ethyl N-Methoxycarbonyl-3-aza-8- (benzyloxycarbonylmethylene)bicyclo[3.3.0] octane-2-carboxylate (14)

A mixture of sodium hydride (0.94 g, 60% dispersion in mineral oil) in tetrahydrofuran (100 ml) was treated with diethyl (benzyloxycarbonylmethyl)phosphonate (9.0 g) under a nitrogen atmosphere. After 1½ hours at room temperature, this solution was treated with a solution of the compound prepared as described in Example 6 (4.0 g) in tetrahydrofuran (30 ml). After an additional two hours, the reaction mixture was poured carefully into water. The resulting mixture was extracted with diethyl ether, and the ether extracts dried over magnesium sulfate and concentrated in vacuo. The title compound was purified by preparative HPLC, eluting with a linear gradient of hexane/ethyl acetate (9:1) to hexane/ethyl acetate (1:1), to give 5.37 g of compound 14 as a mixture of diastereomers.

Mass spectrum (FDMS): m/z=387 (M+).

Analysis calculated for $C_{21}H_{25}NO_6$: C, 65.10; H, 6.50; N, 3.62. Found: C, 64.84; H, 6.57; N, 3.73.

EXAMPLE 12

Preparation of (1SR,2SR,5RS,8SR)-Ethyl N-Methoxycarbonyl-3-aza- 8-(2-hydroxyethyl)bicyclo[3.3.0]octane-2-carboxylate and (1SR,2SR,5RS,8RS)-Ethyl N-Methoxycarbonyl-3-aza-8-(2-hydroxyethyl)bicyclo [3.3.0]octane-2-carboxylate (15)

A mixture of the compound prepared as described in Example 11 (5.30 g) and 5% palladium on carbon (1.5 g) in ethanol (95 ml) was hydrogenated under a hydrogen pressure of 60 psi and at room temperature. After 12 hours, the catalyst was removed by filtration and the filtrate concentrated in vacuo, to give 3.72 g of a yellow oil. This oil was dissolved in tetrahydrofuran (25 ml) and the resulting solution cooled to about 5° C. This cold solution was treated with borane-methyl sulfide complex (12.4 ml, 2M solution in tetrahydrofuran). The resulting mixture was allowed to warm slowly to room temperature over a two hour period. This mixture was carefully added to 1N hydrochloric acid (100 ml). The resulting mixture was extracted with diethyl ether, and the ether extracts dried over magnesium sulfate and concentrated in vacuo. The title compound was purified by preparative HPLC, eluting with a linear gradient of hexane/ethyl acetate (3:1) to hexane/ethyl acetate (1:1), to give 2.63 g of compound 15 as a mixture of diastereomers.

Mass spectrum (FDMS): m/z=286 (M+).

Analysis calculated for $C_{14}H_{23}NO_5$: C, 58.93; H, 8.12; N, 4.91. Found: C, 58.85; H, 8.04; N, 4.92.

EXAMPLE 13

Preparation of (1SR,2SR,5RS,8SR)-Ethyl N-Methoxycarbonyl-3-aza-8-(2-bromoehyl)bicyclo[3.3.0]octane-2-carboxylate and (1SR,2SR,5RS,8RS)-Ethyl N-Methoxycarbonyl-3-aza-8-(2-bromoethyl)bicyclo[3.3.0]octane-2-carboxylate (16)

A solution of triphenylphosphine (3.67 g) in methylene chloride (25 ml) was cooled to 0° C. and treated with bromine until a slight yellow color persisted. Additional triphenylphosphine was added to consume completely the excess bromine, until the solution remained colorless. This solution was treated with a solution of the compound prepared as described in Example 12 (2.0 g) in pyridine (10 ml). After the addition was complete, the reaction mixture was allowed to warm slowly to room temperature. The reaction mixture was added to 1N hydrochloric acid. The title compound was extracted with diethyl ether, and the ether extracts dried over sodium sulfate and concentrated in vacuo. The title compound was purified by preparative HPLC, eluting with a linear gradient of hexane/ethyl acetate (3:1) to hexane/ethyl acetate (1:1), to give 2.3 g of compound 16 as a mixture of diastereomers.

Mass spectrum (FDMS): m/z=347, 349 (M+).

Analysis calculated for $C_{14}H_{22}BrNO_4 \cdot 0.33H_2O$: C, 47.31; H, 6.47; N, 3.94. Found: C, 47.54; H, 6.28; N, 3.53.

EXAMPLE 14

Preparation of (1SR,2SR,5RS,8SR)-Ethyl N-Methoxycarbonyl-3-aza-8-(2-cyanoethyl)bicyclo[3.3.0]octane-2-carboxylate and (1SR,2SR,5RS,8RS)-Ethyl N-Methoxycarbonyl-3-aza-8-(2-cyanoethyl)bicyclo[3.3.0]octane-2-carboxylate (17)

A solution of the compound prepared as described in Example 13 (0.70 g) in dimethyl sulfoxide (5 ml) was treated with finely ground sodium cyanide (0.11 g). The resulting mixture was heated to about 55° C. under a nitrogen atmosphere. After three hours, the reaction mixture was added to 1N sodium hydroxide. The desired compound was extracted with diethyl ether, and the ether extracts dried over sodium sulfate and concentrated in vacuo, to give .57 g of compound 17 as a mixture of diastereomers.

Mass spectrum (FDMS): m/z=294 (M+).

EXAMPLE 15

Preparation of (1SR,2SR,5RS,8SR)-Ethyl N-Methoxycarbonyl-3-aza-8-(2-((2-methoxyethoxy)methoxy)ethyl)bicyclo[3.3.0]octane-2-carboxylate and (1SR,2SR,5RS,8RS)-Ethyl N-Methoxycarbonyl-3-aza-8-(2-((2-methoxyethoxy)methoxy)ethyl)bicyclo[3.3.0]octane-2-carboxylate (18)

A solution of the compound prepared as described in Example 12 (0.57 g) and N,N-diisopropylethylamine (0.31 g) in methylene chloride (10 ml) was cooled to 0° C. and treated with 2-methoxyethoxymethyl chloride (0.30 g). The resulting reaction mixture was allowed to warm slowly to room temperature. After 72 hours, the reaction mixture was added to 1N hydrochloric acid. The desired product was extracted with diethyl ether, and the ether extracts dried over sodium sulfate and concentrated in vacuo, to give 74 g of compound 18 as a mixture of diastereomers.

Mass spectrum (FDMS): m/z=374 (M+H).

Analysis calculated for $C_{18}H_{31}NO_7 \cdot 0.5H_2O$: C, 56.53; H, 8.43; N, 3.66. Found: C, 56.61; H, 8.30; N, 3.35.

EXAMPLE 16

Preparation of (1SR,2SR,5RS,8SR)-Ethyl N-Methoxycarbonyl-3-aza- 8-(2-(cyanomethoxy)ethyl)bicyclo [3.3.0]octane -2-carboxylate and (1SR,2SR,5SR,8RS)-Ethyl N-Methoxycarbonyl-3-aza-8-(2-(cyanomethoxy)ethyl)bicyclo[3.3.0]octane-2-carboxylate (19)

A solution of the compound prepared as described in Example 15 (0.71 g) in methylene chloride (15 ml) was cooled to about 5° C. and sequentially treated with trimethylsilyl cyanide (0.57 g) and boron trifluoride etherate (58 μL). The reaction mixture was allowed to warm slowly to room temperature. After an additional 14 hours, the reaction was added to 1N sodium hydroxide. The desired compound was extracted with diethyl ether, and the ether extracts dried over sodium sulfate and concentrated in vacuo. The title compound was purified by PC-TLC, eluting with hexane/ethyl acetate (7:3), to give 0.48 g of compound 19 as a mixture of diastereomers.

Mass spectrum (FDMS): m/z=324 (M+).

EXAMPLE 17

Preparation of (1SR,2SR,5RS,8SR)-3-Aza-8-(2-carboxyethyl)bicyclo[ 3.3.0]octane-2-carboxylic Acid and (1SR,2SR,5RS,8RS)-3-Aza-8-(2-carboxyethyl)bicyclo[ 3.3.0]octane-2-carboxylic Acid (20)

The title compound was prepared from compound 17 (0.62 g) using the procedure substantially as described in Example 10. Crystallization of the crude product mixture from ethanol/water gave 0.40 g of title compound 20 as a mixture of diastereomers.

Mass spectrum (FDMS): m/z=228 (M+H).

Analysis calculated for $C_{11}H_{17}NO_4$: C, 58.14; H, 7.54; N, 6.16. Found: C, 58.40; H, 7.54; N, 6.38.

EXAMPLE 18

Preparation of
(1SR,2SR,5RS,8SR)-3-Aza-8-(2-(1(2)H-tetrazol-
5-yl)ethyl)bicyclo[3.3.0]octane-2-carboxylic Acid
and
(1SR,2SR,5RS,8RS)-3-Aza-8-(2-(1(2)H-tetrazol-5-yl)
ethyl)bicyclo[ 3.3.0]octane-2-carboxylic Acid (21)

The title compound was prepared from compound 17 (0.54 g) using the procedure substantially as described in Example 9. Crystalization of the crude product mixture from ethanol/water gave 0.32 g of compound 21 as a mixture of diastereomers.

Mass spectrum (FDMS): m/z=252 (M+H).

Analysis calculated for $C_{11}H_{17}N_5O_2 \cdot 0.5EtOH$: C, 52.54; H, 7.35; N, 25.53. Found: C, 52.42; H, 7.03; N, 25.14.

EXAMPLE 19

Preparation of
(1SR,2SR,5RS,8SR)-3-Aza-8-(2-(1(2)H-tetrazole-
5-thio) ethyl)bicyclo[3.3.0]octane-2-carboxylic Acid
and (1SR,2SR,5RS,8RS)-3-Aza-8-(2-(1(2)
H-tetrazole-5-thio) ethyl)bicyclo[
3.3.0]octane-2-carboxylic Acid (22)

A solution of the compound prepared as described in Example 13 (0.50 g), N,N-diisopropylethylamine (0.56 g), and thiotetrazole (0.22 g) in acetonitrile (10 ml) was warmed to about 65° C. under a nitrogen atmosphere. After three hours, the reaction solution was added to 1N hydrochloric acid, and the resulting mixture extracted with diethyl ether. The ether extracts were combined, dried over sodium sulfate, and concentrated in vacuo. The residue was treated with 6N hydrochloric acid (20 ml), and resulting mixture heated to reflux. After 14 hours, the reaction mixture was allowed to cool to room temperature and extracted with diethyl ether. The aqueous phase was concentrated in vacuo. The title compound was purified by cation exchange chromatography (DOWEX 50 X8-100), eluting with 5% pyridine/water. The fractions containing the title compound were combined and evaporated to dryness. The residue was crystalized from ethanol/water to give 0.28 g of compound 22 as a mixture of diastereomers.

Mass spectrum (FDMS): m/z=284 (M+H).

Analysis calculated for $C_{11}H_{17}N_5O_2S$: C, 46.63; H, 6.05; N, 24.72. Found: C, 46.39; H, 6.23; N, 24.48.

EXAMPLE 20

Preparation of
(1SR,2SR,5RS,8SR)-3-Aza-8-(2-(1(2)H-tetrazol-
5-ylmethoxy)
ethyl)bicyclo[3.3.0]octane-2carboxylic Acid and
(1SR,2SR,5RS,8RS)-3-Aza-8-(2-(1(2)H-tetrazol-
5-ylmethoxy)
ethyl)bicyclo[3.3.0]octane-2-carboxylic Acid (23)

The title compound was prepared from compound 19 (0.46 g) using the procedure substantially as described in Example 9. Crystallization of the crude product from ethanol/water gave 0.28 g of compound 23 as a mixture of diastereomers.

Mass spectrum (FDMS): m/z=282 (M+H).

Analysis calculated for $C_{12}H_{19}N_5O_3 \cdot 0.5EtOH$: C, 51.30; H, 7.29; N, 23.01. Found: C, 51.35; H, 7.11; N, 22.97.

EXAMPLE 21

Preparation of (1SR,2SR,5RS,8SR)-Ethyl
N-Methoxycarbonyl-3-aza-8-hydroxybicyclo[3.3.0]
octane-2-carboxylate and
(1SR,2SR,5RS,8RS)-Ethyl
N-Methoxycarbonyl-3-aza-8-hydroxybicyclo
[3.3.0]octane-2-carboxylate (24)

A solution of the compound prepared as described in Example 6 (1.5 g) in ethanol (70 ml) was cooled to 0° C. and treated with sodium borohydride (0.67 g). The resulting reaction mixture was allowed to warm to room temperature. After about 18 hours, the reaction mixture was added carefully to 1N hydrochloric acid, and the resulting mixture extracted with diethyl ether. The ether extracts were combined, dried over magnesium sulfate, and concentrated in vacuo. The title compound was purified by PC-TLC, eluting with a gradient of hexane/ethyl acetate (9:1) to hexane/ethyl acetate (1:1), to give 0.58 g of compound 24 as a mixture of diastereomers.

Mass spectrum (FDMS): m/z=257 (M+).

Analysis calculated for $C_{12}H_{19}NO_5$: C, 56.02; H, 7.44; N, 5.44. Found: C, 55.90; H, 7.32; N, 5.18.

EXAMPLE 22

Preparation of (1SR,2SR,5RS,8SR)-Ethyl
N-Methoxycarbonyl-3-aza- 8-((2-methoxyethoxy
)methoxy)bicyclo[3.3.0]octane-carboxylate and
(1SR,2SR,5RS,8RS)-Ethyl
N-Methoxycarbonyl-3-aza-8-((2-methoxyethoxy)
methoxy)bicyclo[3.3.0]octane-carboxylate (25)

A mixture of the compound prepared as described in Example 21 (0.50 g), N,N-diisopropylethylamine (0.75 g), and 2-methoxyethoxymethyl chloride (0.49 g) in dry methylene chloride (50 ml) was heated to reflux. After about 18 hours, the reaction mixture was allowed to cool to room temperature and added to 1N hydrochloric acid. This mixture was extracted with diethyl ether, and the ether extracts dried over magnesium sulfate and concentrated in vacuo. The title compound was purified by PC-TLC, eluting with a gradient of hexane/ethyl acetate (9:1) to hexane/ethyl acetate (1:2), to give 0.60 g of compound 25 as a mixture of diastereomers.

Mass spectrum (FDMS): m/z=345 (M+).

Analysis calculated for $C_{16}H_{27}NO_7$: C, 55.64; H, 7.88; N, 4.05. Found: C, 55.38; H, 7.81; N, 4.02 .

EXAMPLE 23

Preparation of (1SR,2SR,5RS,8SR)-Ethyl
N-Methoxycarbonyl-3-aza-
8-(cyanomethoxy)bicyclo[3.3.0]octane-2-carboxylate
and (1SR,2SR,5RS,8RS)-Ethyl
N-Methoxycarbonyl-3-aza-8-(cyanomethoxy)bicyclo
[3.3.0]octane-2-carboxylate (26)

A solution of the compound prepared as described in Example 22 (0.60 g) in methylene chloride (35 ml) was cooled to 0° C., and sequentially treated with trimethylsilyl cyanide (0.56 g) and boron trifluoride etherate (0.14 g). The resulting reaction mixture was allowed to warm slowly to room temperature. After about 18 hours, the reaction mixture was added to 1N sodium hydroxide and extracted with diethyl ether. The combined ether extracts were dried over potassium carbonate, filtered, and concentrated in vacuo. The title compound was purified by PC-TLC, eluting with a gradient of hexane/ethyl acetate (9:1) to hexane/ethyl acetate (1:1), to give 0.36 g of compound 26 as a mixture of diastereomers.

Mass spectrum (FDMS): m/z=296 (M+).

Analysis calculated for $C_{14}H_{20}N_2O_5$: C, 56.75; H, 6.80; N, 9.45. Found: C, 57.05; H, 6.66; N, 9.33.

EXAMPLE 24

Preparation of
(1SR,2SR,5RS,8SR)-3-Aza-8-((1(2)H-tetrazol-5-yl)
methoxy)bicyclo[3.3.0]octane-2-carboxylic Acid
and
(1SR,2SR,5RS,8RS)-3-Aza-8-((1(2)H-tetrazol-5-yl)
methoxy)bicyclo[3.3.0] octane-2-carboxylic Acid
(27)

The title compound was prepared from compound 26 (.31 g) using the procedure substantially as described in Example 9. Crystallization of the product from ethanol/water gave .10 g of compound 27 as a mixture of diastereomers.

Mass spectrum (FDMS): m/z=254 (M+H).

Analysis calculated for $C_{10}H_{15}N_5O_3$: C, 47.43; H, 5.97; N, 27.65. Found: C, 47.35; H, 6.00; N, 27.37.

EXAMPLE 25

Preparation of (1SR,2RS,5SR)-Ethyl
N-Methoxycarbonyl-3-aza-8-methylenebicyclo[3.3.0]
octane-2-carboxylate (28)

A suspension of methyltriphenylphosphonium bromide (11.34 g) in tetrahydrofuran (250 ml) was cooled to about 5° C., and treated with a solution of potassium bis(trimethylsilyl)amide in toluene (51 ml of a 0.5M solution). After one hour, this mixture was treated with a solution of the compound prepared as described in Example 6 (5.40 g) in tetrahydrofuran (125 ml). After an additional four hours at about 5° C., the reaction was treated with 1N hydrochloric acid. The resulting mixture was extracted with diethyl ether, and the ether extracts dried over magnesium sulfate and concentrated in vacuo. The title compound was purified by preparative HPLC, eluting with a linear gradient of hexane/ ethyl acetate (9:1) to hexane/ethyl acetate (1:1), to give 4.62 g of compound 28.

Mass spectrum (FDMS): m/z=253 (M+).

Analysis calculated for $C_{13}H_{19}NO_4$: C, 61.64; H, 7.56; N, 5.53. Found: C, 61.55; H, 7.43; N, 5.41.

EXAMPLE 26

Preparation of (1SR,2SR,5RS,8SR)-Ethyl
N-Methoxycarbonyl-3-aza-8-(hydroxymethyl)bicylo
[3.3.0]octane-2-carboxylate and
(1SR,2SR,5RS,8RS)-Ethyl
N-Methoxycarbonyl-3-aza-8-(hydroxymethyl)bicylo
[ 3.3.0]octane-2-carboxylate (29)

A solution of the compound prepared as described in Example 25 (0.85 g) in tetrahydrofuran (50 ml) was cooled to about 0° C. under a nitrogen atmosphere, and treated with a 2.0M solution of borane-methyl sulfide complex in tetrahydrofuran (1.65 ml). After two hours at a temperature of about 0° C. to about 5° C., a 1N sodium hydroxide solution (10 ml) was added cautiously, followed immediately by 30% hydrogen peroxide (5 ml). The resulting mixture was stirred at about 5° C. for an additional hour, then added to 1N hydrochloric acid. The resulting mixture was extracted with diethyl ether, and the combined ether extracts dried over magnesium sulfate and concentrated in vacuo. The title compound was purified by PC-TLC, eluting with a gradient of hexane/ethyl acetate (2:1) to hexane/ethyl acetate (1:2), to give 0.39 g of compound 29 as a mixture of diastereomers.

Mass spectrum (FDMS): m/z=271 (M+).

Analysis calculated for $C_{13}H_{21}NO_5$: C, 57.55; H, 7.80; N, 5.16. Found: C, 57.43; H, 7.91; N, 5.23.

EXAMPLE 27

Preparation of (1SR,2SR,5RS,8SR)-Ethyl
N-Methoxycarbonyl-3-aza-8-(bromomethyl)bicyclo
[3.3.0]octane-2-carboxylate 30)

A solution of triphenylphosphine (2.59 g) in methylene chloride (40 ml) was cooled to 0° C. and treated with bromine until a faint yellow color persisted. Additional triphenylphosphine was added to consume the excess bromine, until the solution remained colorless. This solution was treated with a solution of the compound prepared as described in Example 26 (1.55 g) in pyridine (10 ml). On completion of addition, the ice/water bath was removed and the reaction mixture allowed to warm to room temperature. After one hour, the reaction mixture was added to 1N hydrochloric acid. The resulting mixture was extracted with diethyl ether, and the combined ether extracts dried over magnesium sulfate and concentrated in vacuo. The title compound was purified by preparative HPLC, eluting with a gradient of hexane/ethyl acetate (9:1) to hexane/ethyl acetate (1:1), to give 1.87 g of compound 30.

Mass spectrum (FDMS): m/z=333, 335 (M+).

Analysis calculated for $C_{13}H_{20}BrNO_4$: C, 46.72; H, 6.03; N, 4.19. Found: C, 46.80; H, 6.15; N, 3.95.

EXAMPLE 28

Preparation of (1SR,2SR,5RS,8RS)-Ethyl
N-Methoxycarbonyl-3-aza- 8-
(cyanomethyl)bicyclo[3.3.0]octane-2-carboxylate
(31)

A mixture of the compound prepared as described in Example 27 (1.0 g) and sodium cyanide (.44 g) in anhydrous dimethyl sulfoxide (30 ml) was heated to about 55° C. After about 18 hours, the reaction mixture was diluted with water. The resulting mixture was extracted with diethyl ether, and the combined ether extracts dried over potassium carbonate and concentrated in vacuo. The title compound was purified by PC-TLC, eluting with a gradient of hexane/ethyl acetate (9:1) to hexane/ethyl acetate (1:1), to give 0.75 g of compound 31.

Mass spectrum (FDMS): m/z=280 (M+).

Analysis calculated for $C_{14}H_{20}N_2O_4$: C, 59.99; H, 7.19; N, 9.99. Found: C, 59.74; H, 7.09; N, 9.82.

EXAMPLE 29

Preparation of (1SR,2SR,5RS,8SR)-3-Aza-8-((1
(2)H-tetrazole-5-thio)methyl)bicyclo[3.3.0]
octane-2-carboxylic Acid (32)

The title compound (0.21 g) was prepared from compound (0.7 g) using the procedure substantially as described in Example 9.

Mass spectrum (FDMS): m/z=270 (M+H).

Analysis calculated for $C_{10}H_{15}N_5O_2S$: C, 44.60; H, 5.61; N, 26.00. Found: C, 44.50; H, 5.49; N, 25.77.

EXAMPLE 30

Preparation of (1SR,2SR,5RS,8RS)-3-Aza-8-((1(2)H-tetrazol-5-yl)methyl)bicyclo[3.3.0]octane-2-carboxylic Acid (33)

The title compound was prepared from compound 31 (.45 g) using the procedure substantially as described in Example 9. Crystallization of the crude product from ethanol/water gave 0.20 g of compound 33.

Mass spectrum (FDMS): m/z=238 (M+H).

Analysis calculated for $C_{10}H_{15}N_5O_2$: C, 50.62; H, 6.37; N, 29.52. Found: C, 50.47; H, 6.42; N, 29.70.

EXAMPLE 31

Preparation of (1SR,2SR,5RS,8RS)-Ethyl N-Benzyloxycarbonyl-3-aza-8-(cyanomethyl)bicyclo[3.3.0]octane-6-one-2-carboxylate (34)

A solution of trimethylsilylacetonitrile (2.26 g) in tetrahydrofuran under a nitrogen atmosphere was cooled to about −78° C., and treated with a 1M solution of lithium bis(trimethylsilyl)amide in tetrahydrofuran (20 ml). After 30 minutes at about −78° C., this solution was treated with a solution of the compound prepared as described in Example 2 (3.29 g) in tetrahydrofuran (30 ml). After an additional hour at about −78° C., the reaction mixture was added to saturated aqueous ammonium chloride. The resulting mixture was extracted with diethyl ether, and the combined ether extracts concentrated in vacuo. The residue was dissolved in 10% acetonitrile/water (50 ml). The resulting solution was treated with cesium fluoride (300 mg). After one hour at room temperature, this reaction mixture was added to saturated aqueous sodium bicarbonate solution. The resulting mixture was extracted with diethyl ether, and the combined ether extracts dried over magnesium sulfate and concentrated in vacuo. The title compound was purified by preparative HPLC, eluting with a linear gradient of hexane/ethyl acetate (4:1) to hexane/ethyl acetate (2:3), to give 3.62 g of compound 34.

Mass spectrum (FDMS): m/z=370 (M+).

Analysis calculated for $C_{20}H_{22}N_2O_5$: C, 64.85; H, 5.99; N, 7.56. Found: C, 64.70; H, 5.94; N, 7.38.

EXAMPLE 32

Preparation of (1SR,2SR,5RS,6SR,8RS)-Ethyl N-Benzyloxycarbonyl- 3-aza-8-(cyanomethyl)bicyclo[3.3.0]octane-6-ol-2-carboxylate and (1SR,2SR,5RS,6RS,8RS)-Ethyl N-Benzyloxycarbonyl-3-aza-8-(cyanomethyl)bicyclo[3.3.0]octane-6-ol-2-carboxylate (35)

A solution of the compound prepared as described in Example 31 (2.23 g) in ethanol (50 ml) was cooled to 0° C. and treated with sodium borohydride (.23 g). The resulting mixture was allowed to warm to room temperature. After one hour, the reaction mixture was added to water. The resulting mixture was extracted with diethyl ether, and the combined ether extracted dried over magnesium sulfate and concentrated in vacuo to give 2.23 g of compound 35 as a mixture of diastereomers.

Mass spectrum (FDMS): m/z=372 (M+).

Analysis calculated for $C_{20}H_{24}N_2O_5$: C, 64.50; H, 6.50; N, 7.52. Found: C, 64.65; H, 6.42; N, 7.51.

EXAMPLE 33

Preparation of (1SR,2SR,5RS,6SR,8RS)-Ethyl N-Benzyloxycarbonyl-3-aza-6-bromo-8-(cyanomethyl)bicyclo[3.3.0]octane-2-carboxylate and (1SR,2SR,5RS,6RS,8RS)-Ethyl N-Benzyloxycarbonyl-3-aza-6-bromo-8-(cyanomethyl)bicyclo[3.3.0]octane-2-carboxylate (36)

A solution of triphenylphosphine (2.17 g) in methylene chloride (30 ml) was cooled to 0° C. and treated with bromine until a slight yellow color persisted. Additional triphenylphosphine was added to this solution to consume the excess bromine, until the solution was colorless. This solution was treated with a solution of the compound prepared as described in Example 32 (2.05 g) in pyridine (20 ml). Upon completion of the addition, the reaction mixture was allowed to warm slowly to room temperature. This reaction was added to 1N hydrochloric acid. The resulting mixture was extracted with diethyl ether, and the combined ether extracts dried over magnesium sulfate and concentrated in vacuo. The title compound was purified by preparative HPLC, eluting with hexane/ethyl acetate (3:2), to give two diastereomeric products. The first diastereomer to elute is 36A (1.45 g) and the second diastereomer to elute is 365(.82 g).

Compound 36A

Mass spectrum (FDMS): m/z=434, 436 (M+).

Analysis calculated for $C_{20}H_{23}BrN_2O_4$: C, 55.18; H, 5.33; N, 6.43. Found: C, 55.36; H, 5.31; N, 6.32.

Compound 36B

Mass spectrum (FDMS): m/z=434, 436 (M+).

Analysis calculated for $C_{20}H_{23}BrN_2O_4$: C, 55.18; H, 5.33; N, 6.43. Found: C, 55.39; H, 5.46; N, 6.45.

EXAMPLE 34

Preparation of (1SR,2SR,5RS,8SR)-Ethyl N-Methoxycarbonyl-3-aza-8-(cyanomethyl)bicyclo[3.3.0]octane-2-carboxylate (37)

A mixture of the diastereomers prepared as described in Example 33 (1.70 g) and 1,8-diazabicyclo[5.4.0]undec-7-ene (3.98 g) was heated to about 80° C. under a nitrogen atmosphere. After three hours, the reaction mixture was added to 1N hydrochloric acid. The resulting mixture was extracted with diethyl ether, and the combined ether extracts dried over magnesium sulfate and concentrated in vacuo. The residue (1.40 g) was dissolved in tetrahydrofuran (95 ml) and treated with dimethylpyrocarbonate (2.64 g) and 5% palladium on barium sulfate (1.4 g). The resulting mixture was hydrogenated at a hydrogen pressure of 60 psi and at room temperature. After two hours, the catalyst was removed by filtration and the filtrate concentrated in vacuo. The title compound was purified by PC-TLC, eluting with a gradient of hexane/ethyl acetate (4:1) to hexane/ethyl acetate (1:1), to give 1.01 g of compound 37.

Mass spectrum (FDMS): m/z=280 (M+).

C, 59.99; H, 7.19; N, 9.99. Found: C, 59.77; H, 7.27; N, 9.91.

EXAMPLE 35

Preparation of (1SR,2SR,5RS,8SR)-3-Aza-8-((1(2)H-tetrazol-5-yl)methyl)bicyclo[3.3.0]octane-2-carboxylic Acid (38)

The title compound was prepared from compound 37 (.78 g) using the procedure substantially as described in Example 9.

Analysis calculated for $C_{10}H_{15}N_5O_2 \cdot 0.67H_2O$: C, 48.17; H, 6.61; N, 28.09. Found: C, 48.15; H, 6.66; N, 28.40.

I claim:

1. A compound of the formula

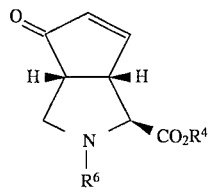

VI wherein:

$R^4$ is $C_1$–$C_6$ alkyl; $C_1$–$C_6$ alkyl substituted by one or more of hydroxy, fluoro, chloro, bromo and iodo; $C_3$–$C_7$ cyclic alkyl; or phenyl ($C_1$–$C_4$)alkyl in which the phenyl group is unsubstituted or is substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl; and $R^6$ is formyl; ($C_1$–$C_6$ alkyl)carbonyl; ($C_1$–$C_6$ alkoxy)carbonyl; phenyloxycarbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl; or phenyl($C_1$–$C_6$ alkoxy)carbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl.

2. The compound of claim 1 wherein $R^4$ is $C_1$–$C_6$ alkyl or phenyl ($C_1$–$C_4$)alkyl in which the phenyl group is unsubstituted or is substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl, and $R^6$ is ($C_1$–$C_6$ alkoxy)carbonyl or phenyl ($C_1$–$C_6$ alkoxy)carbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl.

3. The compound of claim 2 wherein $R^4$ is ethyl and $R^6$ is benzyloxycarbonyl.

4. A compound of the formula

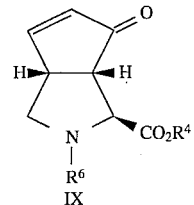

IX wherein:

$R^4$ is $C_1$–$C_6$ alkyl, $C_1$–$C_6$ alkyl substituted by one or more of hydroxy, fluoro, chloro, bromo and iodo; $C_3$–$C_7$ cyclic alkyl; or phenyl($C_1$–$C_4$)alkyl in which the phenyl group is unsubstituted or is substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl; and $R^6$ is formyl; ($C_1$–$C_6$ alkyl)carbonyl; ($C_1$–$C_6$ alkoxy)carbonyl, phenyloxycarbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl; or phenyl($C_1$–$C_6$ alkoxy)carbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl.

5. The compound of claim 4 wherein $R^4$ is $C_1$–$C_6$ alkyl or phenyl ($C_1$–$C_4$)alkyl in which the phenyl group is unsubstituted or is substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl, and $R^6$ is ($C_1$–$C_6$ alkoxy)carbonyl or phenyl ($C_1$–$C_6$ alkoxy)carbonyl in which the phenyl group is unsubstituted or substituted with one or two moieties chosen from the group consisting of halogen, hydroxy, cyano, nitro, $C_1$–$C_6$ alkyl, $C_1$–$C_4$ alkoxy, ($C_1$–$C_6$ alkoxy)carbonyl, carboxymethyl, hydroxymethyl, amino, aminomethyl and trifluoromethyl.

6. The compound of claim 5 wherein $R^4$ is ethyl and $R^6$ is benzyloxycarbonyl.

* * * * *